(12) United States Patent
Ornath et al.

(10) Patent No.: US 7,487,689 B2
(45) Date of Patent: Feb. 10, 2009

(54) CONTAMINANT SCANNING SYSTEM

(75) Inventors: Fredy Ornath, Tel-Aviv (IL); Robert Roach, Ramat-Hasharon (IL)

(73) Assignee: Tracetrack Technology Ltd., Petach-Tikva (IL)

(*) Notice: Subject to any disclaimer, the term of this patent is extended or adjusted under 35 U.S.C. 154(b) by 0 days.

(21) Appl. No.: 10/542,426

(22) PCT Filed: Jan. 7, 2004

(86) PCT No.: PCT/IL2004/000011

§ 371 (c)(1),
(2), (4) Date: Jul. 13, 2005

(87) PCT Pub. No.: WO2004/063697

PCT Pub. Date: Jul. 29, 2004

(65) Prior Publication Data

US 2006/0060006 A1    Mar. 23, 2006

Related U.S. Application Data

(63) Continuation-in-part of application No. PCT/IL03/00041, filed on Jan. 15, 2003.

(51) Int. Cl.
G01N 1/00 (2006.01)
(52) U.S. Cl. ................................... 73/864.33
(58) Field of Classification Search .............. 73/864.33
See application file for complete search history.

(56) References Cited

U.S. PATENT DOCUMENTS

| | | | |
|---|---|---|---|
| 2,329,055 A * | 9/1943 | Kegan | 229/80 |
| 2,832,545 A | 4/1958 | Benjamin | |
| 3,736,792 A * | 6/1973 | Poulsen | 73/25.03 |
| 3,741,820 A | 6/1973 | Hebel et al. | |
| 3,942,357 A | 3/1976 | Jenkins | |
| 3,985,017 A | 10/1976 | Goldsmith | |
| 3,998,101 A | 12/1976 | Bradshaw et al. | |
| 4,381,673 A | 5/1983 | Klauba et al. | |
| 4,422,334 A | 12/1983 | Yasuda | |
| 4,483,261 A | 11/1984 | Green et al. | |
| 4,580,440 A | 4/1986 | Reid et al. | |
| 4,718,268 A | 1/1988 | Reid et al. | |

(Continued)

FOREIGN PATENT DOCUMENTS

GB    1 439 706    6/1976

(Continued)

OTHER PUBLICATIONS

Otani, Y. et al.; "Removal of Fine Particles From Smooth Flat Surfaces by Consecutive Pulse Air Jets;" Aerosol Science Technology; vol. 23; 1995; pp. 665-673.

(Continued)

Primary Examiner—Robert R Raevis

(57) ABSTRACT

A vapor collection system. The system includes one or more walls that define a chamber for receiving inspected items, at least one pipe adapted to eject a gas jet within the chamber, the gas jet being provided at an angle relative to a normal to the wall of the chamber, at the point at which the pipe enters the chamber, at least one tube adapted to remove gas samples from the chamber, and an analysis unit adapted to determine whether the gas samples include one or more particulates.

28 Claims, 13 Drawing Sheets

U.S. PATENT DOCUMENTS

| | | | |
|---|---|---|---|
| 4,820,920 A | | 4/1989 | Bather |
| 4,838,877 A | * | 6/1989 | Massau ..................... 604/272 |
| 4,877,433 A | | 10/1989 | Oshitari |
| 4,896,547 A | | 1/1990 | Arney et al. |
| 4,909,089 A | | 3/1990 | Achter et al. |
| 4,909,090 A | | 3/1990 | McGown et al. |
| 4,987,767 A | | 1/1991 | Corrigan et al. |
| 5,092,218 A | | 3/1992 | Fine et al. |
| 5,092,220 A | | 3/1992 | Rounbehler |
| 5,109,691 A | * | 5/1992 | Corrigan et al. ............ 73/23.36 |
| 5,123,274 A | | 6/1992 | Carroll et al. |
| 5,162,652 A | | 11/1992 | Cohen et al. |
| 5,202,023 A | | 4/1993 | Trimmer et al. |
| 5,345,809 A | | 9/1994 | Corrigan et al. |
| 5,642,393 A | | 6/1997 | Krug et al. |
| 5,939,647 A | * | 8/1999 | Chinn et al. ............. 73/864.71 |
| 5,942,699 A | | 8/1999 | Ornath et al. |
| 6,073,499 A | | 6/2000 | Settles |
| 6,074,608 A | * | 6/2000 | Matz ........................... 422/83 |
| 6,324,927 B1 | * | 12/2001 | Ornath et al. ............ 73/864.33 |
| 6,328,647 B1 | | 12/2001 | Traudt ........................ 454/255 |
| 6,334,365 B1 | * | 1/2002 | Linker et al. ............. 73/864.81 |
| 6,408,701 B1 | * | 6/2002 | Fujita ..................... 73/864.71 |
| 6,905,711 B1 | * | 6/2005 | Tullo et al. .................. 424/618 |
| 7,100,461 B2 | * | 9/2006 | Bradley et al. ........... 73/864.33 |
| 2002/0124664 A1 | * | 9/2002 | Call et al. ................. 73/863.22 |
| 2002/0164088 A1 | * | 11/2002 | Collins ........................ 383/10 |
| 2003/0136179 A1 | * | 7/2003 | Felice et al. ................ 73/31.03 |
| 2003/0136203 A1 | * | 7/2003 | Yoon ........................ 73/864.33 |
| 2004/0020267 A1 | * | 2/2004 | Megerle .................... 73/31.03 |
| 2004/0202574 A1 | | 10/2004 | Sapir et al. |
| 2005/0181520 A1 | | 8/2005 | Omath |

FOREIGN PATENT DOCUMENTS

| | | |
|---|---|---|
| WO | WO 97/14033 | 4/1997 |
| WO | WO 03/087777 | 10/2003 |
| WO | WO 2007/007212 | 1/2007 |

OTHER PUBLICATIONS

Otani, Y. et al.; "Removal of Fine Particles From Wafer Surface by Pulse Air Jets;" Kagaku Kogaku Ronbunshu; (1993) 19; pp. 114-119.

Masuda, H. et al.; "The Removal of Particles From Flat Surfaces Using a High-Speed Air Jet;", Advanced Powder Technology; vol. 5; No. 2; 1994; pp. 205-217.

Gotoh, K. et al.; "High-Efficiency Removal of Fine Particles Deposited on a Solid Surface;" J. Soc Powder Tech Jpn; vol. 31; No. 10; 1994; pp. 726-733.

Liu, B. Y. H. et al.; "Development of Particle Standards for Testing Explosive Detection Systems: Characterization of the Adhesion Forces Between Composition 4 Particles and Polyethylene;" SPIE Cargo Inspection Technologies; vol. 2276; 1994; pp. 45-55.

* cited by examiner

US 7,487,689 B2

CONTAMINANT SCANNING SYSTEM

RELATED APPLICATION

The present application is a U.S. National Phase of PCT Application No. PCT/IL2004/000011, filed on Jan. 7, 2004, which is a continuation in part of PCT application PCT/IL03/00041, filed Jan. 15, 2003, the disclosure of which is incorporated herein by reference.

FIELD OF THE INVENTION

The present invention relates to systems for identifying the presence of chemical materials and in particular to screening systems.

BACKGROUND OF THE INVENTION

One method for scanning luggage for illegal materials, such as explosives and drugs, is collecting vapors and small particles (referred to collectively herein as vapors) from the luggage and passing the vapors to a detection system (also known as a trace analyzer) which determines whether the vapors include traces of specific materials.

One type of collection apparatus includes hand held machines, such as described in U.S. Pat. No. 4,909,090 to McGown et al., U.S. Pat. No. 5,092,220 to Rounbehler, and U.S. Pat. No. 5,123,274 to Carroll et al., the disclosures of which documents is incorporated herein by reference. These machines are directed by a human holding the machine to suck air from the surface of inspected luggage. The machines may heat the surface of the luggage and/or direct jets of air at the luggage in order to aid in dislodging vapors from the luggage. These hand held collection apparatus suffer from high cost of operators who need to pass the machine over the luggage and from low accuracy due to collection of only a small portion of the air surrounding the luggage.

Instead of bringing the collection apparatus to the inspected luggage, some systems suggest the use of a swab or brush to remove samples from the luggage. Particles collected by the swab or brush are then provided to the detection system.

Other collection systems include chambers into which the luggage is inserted, such as described in U.S. Pat. Nos. 5,942,699 and 6,324,927 to Ornath et al., U.S. Pat. No. 4,580,440 to Reid et al., U.S. Pat. No. 5,162,652 to Cohen et al., U.S. Pat. No. 3,942,357 to Jenkins et al., U.S. Pat. No. 3,998,101 to Bradshaw et al., the disclosures of which documents is incorporated herein by reference. The luggage is preferably sealed in the chamber and various methods are used to dislodge vapors from the luggage. The air in the chamber is then passed to an inspection system. The volume of air in these chambers is generally too large such that some contaminants having low dilution rates are not detected.

Other collection systems are directed to checking humans and therefore are not sealed. The operation of these systems is similar to that described above, except that there is no airtight seal. Such systems are described, for example, in U.S. Pat. No. 4,909,089 to Achter et al., and U.S. Pat. No. 5,345,809 to Corrigan et al., the disclosures of which documents is incorporated herein by reference.

One of the methods used to dislodge vapors from humans and luggage is air jets directed at the inspected humans or luggage, as described, for example, in U.S. Pat. No. 4,909,089. In some cases it may be desired to avoid directing air jets at humans, especially at their face. U.S. Pat. No. 4,909,089 suggests suppressing air jets directed at the inspected human's face. U.S. Pat. No. 4,987,767 describes a sampling chamber in which air jet streams are injected from a plurality of ducts in different sides of the chamber so as to induce air flow from the floor of the chamber to its ceiling. This air flow sweeps over individuals or objects passing through the chamber. U.S. Pat. No. 6,073,499 to Settles, the disclosure of which is incorporated herein by reference, describes a portal which relies upon the heat of the human body to generate flow of air towards the ceiling of the portal.

SUMMARY OF THE INVENTION

An aspect of some embodiments of the present invention relates to a vapor collection system including an inspection chamber having an adjustable size. Inspected items are placed in the chamber and before causing the release of vapors from the inspected items, the size of the chamber is adjusted to minimize the volume of the chamber.

In some embodiments of the invention, at least some of the walls of the chamber are formed of a flexible mantle, for example of plastic. A pressure difference is optionally formed between the inside and outside of the chamber, such that the flexible mantle conforms to the shape of the inspected items. The pressure difference is optionally substantially constant and relatively small. In some embodiments of the invention, the pressure difference is applied by sustaining a pressure lower than the atmospheric pressure in the chamber. Alternatively or additionally, an external chamber, at a higher pressure, enclosing the inspection chamber is used. Optionally, the walls of the chamber are closely spaced from the inspected items but not touching the items, over at least a portion of the surface of the inspected items. The spacing of the walls from the inspected items prevents the walls from interfering with collecting the vapors.

An aspect of some embodiments of the present invention relates to an automatic position adjustment system, which is used to automatically adjust the position of one or more units of the system which interacts with the inspected items. The one or more units which interact with the inspected items optionally include one or more of suction nozzles, air blowing nozzles, heaters and radiation sources.

In some embodiments of the invention, the one or more units whose positions are adjusted are mounted on walls of a chamber in which the inspected items are inserted and their position is adjusted by changing the positions of the walls of the chamber, for example to conform to the outer contours of the inspected items. Alternatively or additionally, one or more of the units is mounted on a carrier separate from the walls of the chamber. Optionally, the units whose positions are adjusted are located in a hermetically sealed chamber. The adjustment of the positions of the units is optionally performed although the chamber is sealed, in order to limit the amount of air or other gas in the chamber that needs to be processed by the trace analyzer.

An aspect of some embodiments of the present invention relates to a vapor collection system, including an inspection chamber and an external chamber at least partially surrounding the inspection chamber. The external chamber optionally has a controlled and variable gas pressure, such that the relative gas pressure between the inspection chamber and the external chamber is controllable, for example kept constant. In some embodiments of the invention, during a vapor release stage, the pressure within the inspection chamber is varied, while the relative pressure between the inspection chamber and the external chamber is substantially constant.

An aspect of some embodiments of the present invention relates to a method of collecting vapor samples, in which a collection unit is placed in an inspected item without a human holding the collection unit. Optionally, the inspected item is closed with the collection unit inside the inspected item.

Optionally, the collection unit applies one or more vapor release inducement measures, such as mechanical agitation, air jets and/or radiation. In some embodiments of the invention, the collection unit is flexible and is inflated and/or deflated in order to induce agitations in the inspected item. In some embodiments of the invention, the mechanical agitations include direct vibrations applied at a predetermined frequency, for example by an agitation table on which the inspected elements are placed. Alternatively or additionally, the agitations include vibrations at a plurality of different frequencies or agitations of random nature not being at any specific frequency. Such random agitations may be applied to an agitation table by a pneumatic device, such as a piston, controlled by a computer that uses a random number generator to determine the random agitations. Alternatively, any other push and/or pull device may be used to apply the agitations. Alternatively, the agitations may be applied by a hammer which at irregular times pushes the agitation table.

In some embodiments of the invention, the collection unit is included entirely in the inspected item and is not connected to external apparatus, through tubes, wires or a wireless link. Alternatively, the collection unit is connected to wirelessly to an external apparatus. Further alternatively, the collection unit is connected through wires or tubes to an external collection unit. For example, the collection unit optionally does not include a trace analyzer or collection chamber, but rather passes collected vapors to a collection chamber external to the inspected item.

In some embodiments of the invention, the collection unit placed in the inspected item is used in conjunction with a vapor collection system which collects vapors from the outer surface of the inspected item. Alternatively or additionally, the collection unit placed in the inspected item is used in conjunction with a vapor release inducement system, which applies vapor release enhancement measures to the inspected item, from outside of the inspected item.

An aspect of some embodiments of the present invention relates to a method of collecting vapors in which cooperation is achieved between apparatus within inspected items and apparatus outside of the inspected items. Optionally, vapor release measures are applied from at least one of an internal and external vapor unit and gas samples are collected by the other of the internal and external vapor units. Cooperation of an internal and an external unit generally provide more efficient collection of vapors from the inspected item.

An aspect of some embodiments of the present invention relates to a method of collecting vapor samples, in which a vapor release inducement unit, which does not collect vapors, is placed in an inspected item and induces vapor release while vapors are collected from the inspected item by a separate collection unit. Optionally, the separate collection unit is located outside of the inspected item. Alternatively or additionally, a separate collection unit is inserted into the inspected item adjacent the vapor release unit or remote therefrom.

An aspect of some embodiments of the invention relates to a vapor release inducement unit which vibrates within an inspected item. The vapor release inducement unit may optionally also collect vapors from the inspected item. Optionally, the vapor release inducement unit comprises a flexible casing which is inflated and/or deflated to induce vapor release.

An aspect of some embodiments of the invention relates to inducing vapor collection from an item by blowing a gas (e.g., air) jet having a substantial vector portion which is tangential to the inspected items. Optionally, the gas jet hits the inspected item with an angle of less than 60° or even 30° to the surface of the inspected item. In some embodiments of the invention, the gas jet is substantially parallel to a surface of the inspected item, in the proximity of the inspected item. Directing the air jets tangentially to the surface generally achieves a shear gradient and hence causes contaminant release. Directing the air jets with an angle at the inspected item also increases the surface area affected by the air jets.

In some embodiments of the invention, the gas jet is ejected from the pipe at an angle relative to a normal to the wall of the chamber, at the point at which the pipe enters the chamber. It is noted, that in some embodiments of the invention, the pipe ends flush with the inner wall of the chamber and does not protrude into the chamber. In such cases, the point at which the pipe enters the chamber is the point at which the pipe ends. The pipe may enter the chamber in the middle of a substantially flat wall, in which case the normal to the wall is at 90° to the entire surrounding wall. In other cases, the wall may be curved, in which case the normal is at 90° to a surface tangent to the wall. In still other cases, the pipe may enter the chamber at a corner connecting two walls which are perpendicular to each other. In such a case, the normal is at 45° to each of the walls and at 90° to a surface at equal distance from both walls, that passes through the corner. Stated in other words, the gas jets enter the chamber at an angle, such that the jet is not at an equal distance from the wall surrounding the point of entrance.

Optionally, the pipe leading the gas of the jet defines a substantial bend in the path of the gas to be injected as the jet, within the chamber. Optionally, the bend has an angle of at least 30° or even 60°. In some embodiments of the invention, the bend is of 90°, for example from a direction perpendicular to the inspected item to a direction substantially parallel the inspected item. Optionally, the pipe has a Y-shape or a T-shape at its distal end. In an exemplary embodiment of the invention, the pipe within the chamber has a three-dimensional shape having a two-dimensional projection having a T-shape or Y-shape.

Optionally, the distal end of the pipe is positioned close to an inspected item such that the jets of air are directed along a surface of the inspected item rather than being directed at the item.

An aspect of some embodiments of the invention relates to inducing shock waves into an inspection chamber. The shock waves are optionally induced by generating supersonic jets of gas (e.g., air). Optionally, the air in the pipes used to provide the air jets is at a pressure higher than the air pressure within the chamber, such that when the air enters the chamber it expands and generates supersonic shock waves. In some embodiments of the invention, the outlets of the pipes are flared, such that their outlet diameter is greater than their input diameter. The flaring is optionally of an amount sufficient to generate shockwaves with the jet velocities and/or pressures of the jets introduced to the chamber.

In some embodiments of the invention, flared pipe outlets are used also without supersonic jets in order to increase the area covered by the jets.

An aspect of some embodiments of the invention relates to an agitation table of a vapor collection system which moves with irregular movements. Optionally, the irregular movements comprise random movements determined randomly for each inspection session, such that different sessions involve different sequences of irregular movements. Alternatively, the irregular movements comprise pseudo-random movements of a predetermined sequence repeated in each inspection session. Such irregular agitation movements affect the inspected items as if they were vibrated at a plurality of different low frequencies. Thus, the advantage of using a plurality of different frequencies is achieved within a short inspection session.

An aspect of some embodiments of the invention relates to vibrating items in a vapor collection system at a plurality of different frequencies, in order to determine one or more frequencies most suitable for inspecting the items. The determined frequency is optionally used thereafter for the remaining portion of the inspection session of the item. Optionally, the suitable frequencies are resonant frequencies of the inspected item and/or of objects within the inspected item. Using the resonance frequencies ensures that smaller input energies result in more effective agitation.

In some embodiments of the invention, a gage that measures acceleration of the inspected item is placed within the inspected chamber. The readings from the gage are used to determine a vibration frequency at which the acceleration is maximal. Such maximal acceleration is used as an indication of a resonance frequency to be used in the remaining portion of the inspection session.

An aspect of some embodiments of the invention relates to a vapor inspection system in which at least one parameter of its vapor release inducement is controlled by feedback from at least one sensor of the system. Optionally, the feedback is not directly related to the controlled parameter.

In some embodiments of the invention, the at least one sensor includes a pressure or flow sensor which provides indication on the actual application of the release inducement means. Alternatively or additionally, the at least one sensor provides an indication of a property of the inspected item, such as the resonance frequency of the inspected item. Optionally, the sensor comprises a vibration sensor which indicates when the inspected item has maximal vibrations. Further alternatively or additionally, the sensor provides an indication on the amount of particles released from the inspected items. Optionally, the feedback is provided on particles not being searched for, such as dust or another particle generally included in inspected items or a test agent induced for test purposes by the inspection system, for example with air jets entering the inspection chamber. This allows for optimal testing, without the inspected item necessarily including the target material, and/or when only very small amounts of the target material are released under non-optimal conditions.

The at least one parameter controlled responsive to the feedback optionally includes a parameter of applied air jets, such as their angle relative to the inspected items, their pulse rate, and/or their velocity. Alternatively or additionally, the controlled parameter includes a parameter of mechanical agitation, such as a vibration rate of a table carrying the inspected items.

There is therefore provided in accordance with an embodiment of the present invention, a vapor collection system, comprising one or more walls that define a chamber for receiving inspected items, at least one pipe adapted to eject a gas jet within the chamber, the gas jet being provided at an angle relative to a normal to the wall of the chamber, at the point at which the pipe enters the chamber, at least one tube adapted to remove gas samples from the chamber and an analysis unit adapted to determine whether the gas samples include one or more particulates. Optionally, the angle relative to the normal is at least 30° or at least 90°. Optionally, the at least one pipe is placed such that gas passes into the chamber substantially perpendicular to a wall of the chamber, through which the pipe passes into the chamber.

Optionally, the at least one pipe is placed such that gas is ejected from the pipe within the chamber substantially parallel to a wall of the chamber, through which the pipe passes into the chamber. Optionally, the at least one pipe has at least one flared outlet and/or is adapted to eject a super-sonic jet. Optionally, the at least one pipe has a plurality of outlets evenly dispersed around its circumference. Optionally, the at least one pipe has a plurality of outlets unevenly dispersed around its circumference. Optionally, the at least one pipe has an outlet of substantially 360° around its circumference. Optionally, the at least one pipe is adapted to touch an inspected item within the chamber during an inspection session. Optionally, the chamber is adapted to receive the inspected item at a location, such that the at least one pipe is adapted to eject gas jets substantially parallel to a surface of the inspected item.

Optionally, the chamber is adapted to receive the inspected item at a location, such that the at least one pipe extends perpendicular to the item along most of its extent within the chamber. Optionally, the one or more walls comprise one or more mantles. Optionally, the one or more walls are adapted to be moved, such that the volume of the chamber is determined responsive to the size of the inspected item. Optionally, the at least one pipe has a bend of at least 30° within the chamber, for example, a bend of substantially 90°.

There is further provided in accordance with an embodiment of the present invention, a method of collecting vapors from an inspected item, comprising placing an item for inspection within a chamber, blowing a gas jet from a pipe within the chamber, at an angle relative to a normal to a wall of the chamber, at a point at which the pipe enters the chamber, removing gas samples from the vicinity of the item and analyzing the removed gas samples for traces of one or more particulates. Optionally, placing the item in the chamber comprises placing in a chamber defined by a flexible mantle.

There is further provided in accordance with an embodiment of the present invention, a method of collecting vapors from an inspected item, comprising providing an item for inspection, positioning a gas pipe next to the provided item, blowing gas jets from the pipe along a surface of the inspected item tangential to the surface of the item, the gas jets exiting the pipe in a direction tangential to the surface of the item, removing gas samples from the vicinity of the item and analyzing the removed gas samples for traces of one or more particulates. Optionally, positioning the pipe next to the provided item comprises positioning the pipe at a corner of the item. Optionally, positioning the pipe next to the provided item comprises positioning a pipe having a bent head. Optionally, positioning the pipe next to the provided item comprises positioning a portion of the pipe connected to the bent head perpendicular to the item.

There is further provided in accordance with an embodiment of the present invention, a vapor collection system, comprising at least one pipe adapted to provide gas jets toward an inspected item, a gas jet source adapted to generate a gas flow which is ejected by the at least one pipe as a supersonic jet, at least one tube adapted to remove gas samples from a vicinity of the inspected item, and an analysis unit adapted to determine whether the gas samples include one or more particulates. Optionally, the at least one pipe has at least one flared outlet or even at least four flared outlets.

There is further provided in accordance with an embodiment of the present invention, a vapor collection system, comprising a chamber for receiving inspected items, an agitation table adapted to agitate the inspected items, a controller adapted to move the agitation table with at least one of irregular movements and a plurality of different frequencies, at least one tube adapted to remove gas samples from the chamber and an analysis unit adapted to determine whether the gas samples include one or more particulates.

Optionally, the controller is adapted to move the agitation table with irregular movements. Optionally, the controller is adapted to move the agitation table with random movements. Optionally, the controller is adapted to move the agitation table at a plurality of different frequencies. Optionally, the controller is adapted to select a frequency at which the inspected items have a highest amplitude response to the vibrations of the agitation table. Optionally, the controller is adapted to apply vibrations at the selected frequency to the agitation table. Optionally, the vapor collection system comprises a vibration sensor adapted to measure the response of the inspected items to the vibrations.

BRIEF DESCRIPTION OF FIGURES

Particular non-limiting embodiments of the invention will be described with reference to the following description of embodiments in conjunction with the figures. Identical structures, elements or parts which appear in more than one figure are preferably labeled with a same or similar number in all the figures in which they appear, in which.

DETAILED DESCRIPTION OF EXEMPLARY EMBODIMENTS

Figure 1A:
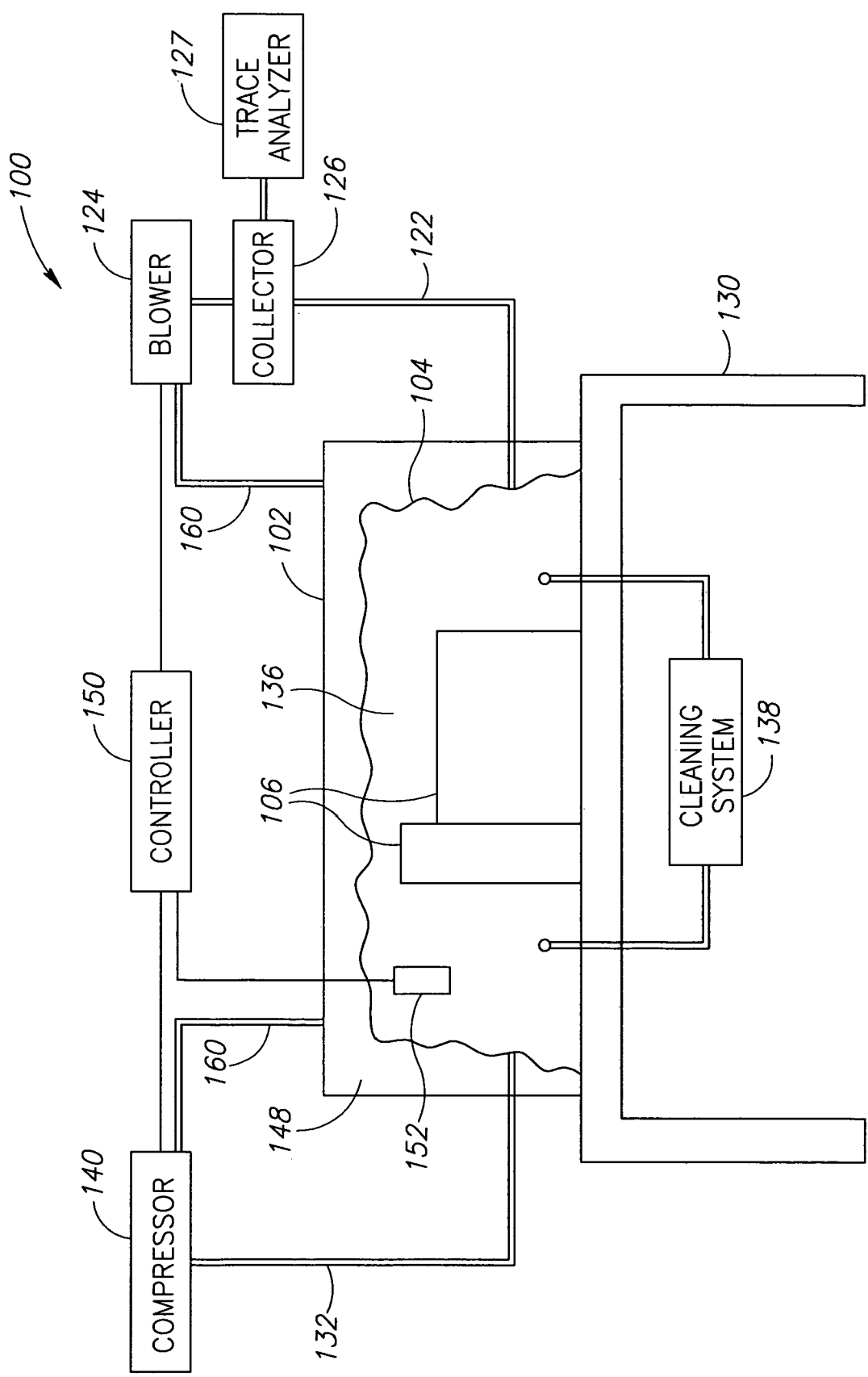
FIGS. 1A and 1B are schematic illustrations of a vapor inspection system, in two different operation states, in accordance with an exemplary embodiment of the invention.
Figure 1B:
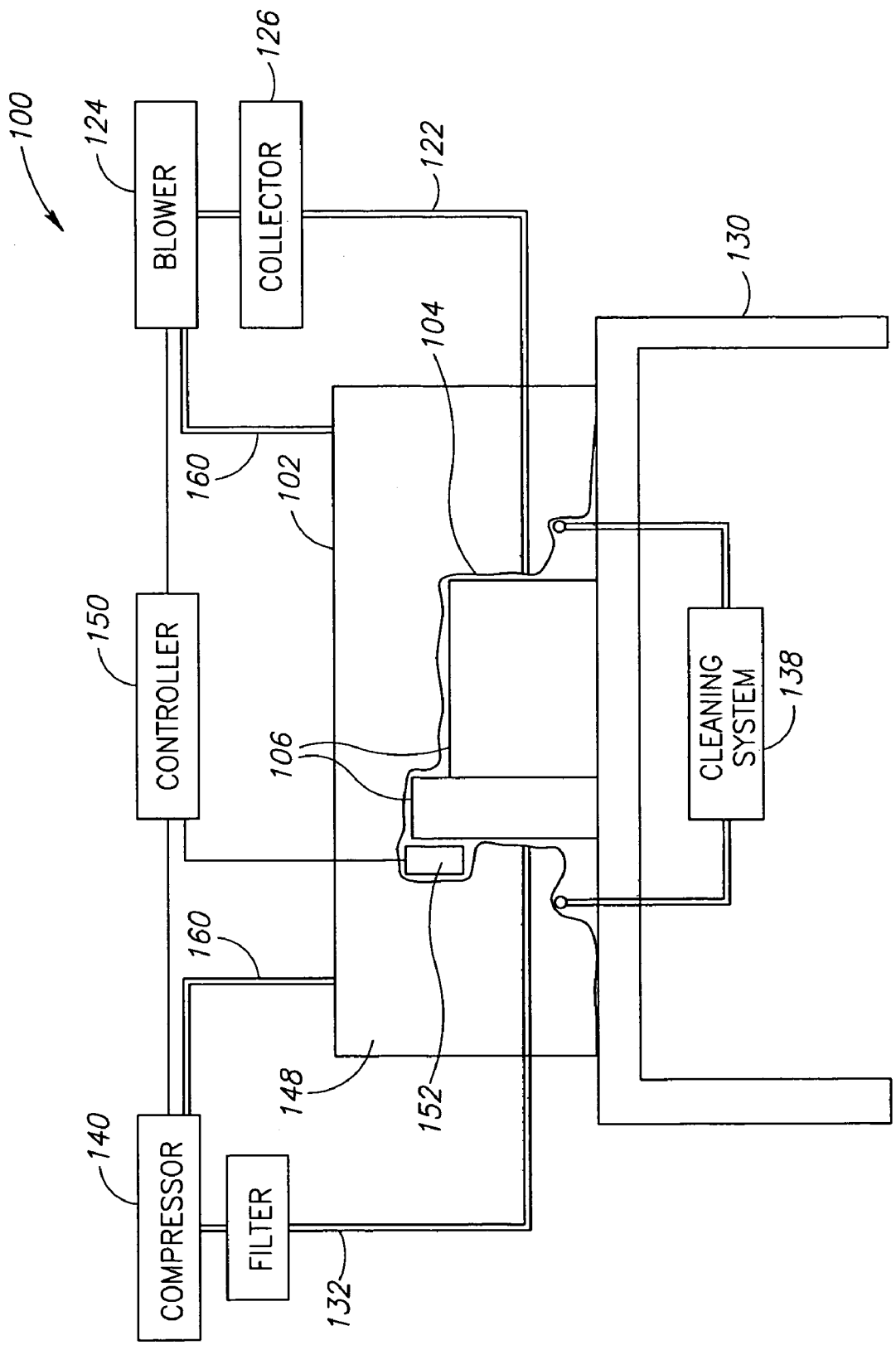

FIGS. 1A and 1B are schematic illustrations of a vapor inspection system 100, in accordance with an exemplary embodiment of the invention. Vapor inspection system 100 optionally includes an external enclosure 102 and a flexible mantle 104 serving as an internal enclosure. In operation, inspected items 106 are inserted into an inspection chamber 136, enclosed by mantle 104, as shown in FIG. 1A. A blower 124 optionally sucks the air out of the inspection chamber 136, through air pipes 122, such that mantle 104 closely fits around inspected items 106, as shown in FIG. 1B. Thereafter, vapor releasing methods are applied to inspected items 106 in order to release vapors from the items, if such vapors are in and/or on inspected items 106. Intermittently, concurrently and/or after the vapor releasing methods are applied, blower 124 optionally sucks air out of the inspection chamber 136 and the sucked air is passed to a collector 126, which accumulates vapors and/or solids for inspection. A trace analyzer 127 analyzes the collected vapors to determine whether they include chemicals that are being searched for.

In some embodiments of the invention, collector 126 comprises a paper filter and/or a scrubber type collector. Alternatively or additionally, any other collection apparatus is used. Trace analyzer 127 is of any type known in the art, for example, as described in U.S. Pat. No. 5,345,809 to Corrigan, et al., the disclosure of which patent is incorporated herein by reference. Trace analyzer 127 optionally operates automatically after an inspection session of system 100 and/or at least partially during the inspection session. Optionally, a user interface displays the names of chemicals which were identified. In some embodiments of the invention, an alarm is operated automatically when at least a predetermined vapor amount of a searched substance is identified. In some embodiments of the invention, trace analyzer 127 is activated after each inspection session of system 100. Alternatively, trace analyzer 127 is activated after a predetermined number of inspection sessions and/or when it is determined to have collected at least a predetermined amount of vapors. Operating trace analyzer 127 for a plurality of inspection sessions reduces the costs of operating trace analyzer 127, at the expense of a less accurate indication of the item in which item the chemicals are contained.

Alternatively to operating automatically, trace analyzer 127 may be activated manually by a human operator. For example, the human operator may determine the frequency of operation of trace analyzer 127 according to a suspiciousness level of the inspected items. Alternatively to trace analyzer 127 being connected to collector 126, collector 126 is removed from system 100 after one or more inspection sessions and is placed in a trace analyzer 127 for analysis. Further alternatively or additionally, a plurality of different trace analyzers, optionally searching for different chemicals, are used. Further alternatively or additionally, system 100 does not include a collector and the sucked gas from chamber 136 is provided directly to analyzer 127.

In some embodiments of the invention, a compressor 140 pumps air into inspection chamber 136, for example through air pipes 132, while blower 124 sucks out air for vapor inspection, in order to keep the pressure within inspection chamber 136 constant. Compressor 140 may be implemented together with blower 124 in the same apparatus or may be implemented in separate apparatus. Alternatively, high pressure air is provided from an external high pressure line and compressor 140 is not used or is used as a backup.

Optionally, the air pressure within inspection chamber 136 is set such that mantle 104 does not touch and/or crush inspected items 106, while keeping the air volume within inspection chamber 136 minimal. In some embodiments of the invention, the volume of chamber 136 is not more than 20%, 10% or even 5% above the volume of inspected items 106. Alternatively or additionally, the empty volume of chamber 136 is not greater than a predetermined air volume, for example not more than 1-2 liters. Keeping the air volume at a minimal level prevents dilution of vapors extracted from the inspected items, dilution which may make the identification of illegal materials more difficult.

FIG. 1A further illustrates a table 130 on which inspected items 106 are placed. In some embodiments of the invention, table 130 may be vibrated in order to induce vapor release, as described, for example, in the above mentioned U.S. Pat. Nos. 5,942,699 and 3,942,357. In some embodiments of the invention, table 130 is vibrated at a predetermined frequency, for example between 1-10 cycles per second. Alternatively, table 130 is vibrated irregularly so as to increase the chances that at least one of the different jolts will release contaminants which it is desired to detect. Alternatively or additionally, during an inspection session, table 130 is vibrated at a plurality of different frequencies in order to identify one or more frequencies best suited to release contaminants from the inspected item or items. Thereafter, table 130 is vibrated at the identified frequency for a longer period.

In some embodiments of the invention, the suitability of the frequencies is identified according to the responsiveness of the vibration of the inspected items 106, for example using methods described in U.S. Pat. No. 4,381,673 to Klauba et al., and/or in U.S. Pat. No. 3,741,820 to Hebel et al., the disclosures of which are incorporated herein by reference. Alternatively or additionally, the suitability of the frequencies is measured by a particle release sensor which determines the amount of particles being released.

Alternatively to table 130, any other base may be used for placement of inspected items 106. In some embodiments of the invention, a portion of a conveyor belt is used as a base. Inspected items may be mounted along the entire conveyor belt, while chamber 136 is formed over a portion of the conveyor belt. Optionally, before operation, mantle 104 is lifted, and a group of one or more inspected items is allowed to enter beneath the mantle. Mantle 104 is then lowered and optionally attached to the base to minimize or prevent escape of air. System 100 is then activated as described above. Thereafter, mantle 104 is lifted and the conveyor belt is moved to change the inspected items 106 beneath the mantle. In some embodiments of the invention, mantle 104 is replaced after each inspection or every predetermined number of items, for example for cleaning.

The conveyor belt may have a circular track such that items not removed from the conveyor belt repeatedly enter the inspection chamber or the conveyor belt may have a beginning point at which items are loaded and an end point where inspected items are unloaded. Alternatively or additionally, the conveyor belt moves in a first direction for loading items and in the opposite direction for unloading the items and the same point is used for loading and unloading items.

In some embodiments of the invention, the portions of the conveyor belt on which inspected items 106 are placed are elevated relative to the remaining portions of the conveyor belt. The elevated portion is optionally of a predetermined shape in which a bottom portion of mantle 104 fits. In some embodiments of the invention, a bottom portion of mantle 104 is rigid and fits onto the elevated portion in a sealed manner.

The conveyor belt and/or table 130 may be impermeable to gases, such that a separate mantle base is not required. Alternatively or additionally, mantle 104 and/or a separate mantle piece may surround the inspected item from below. Further alternatively, a rigid chamber closing element, optionally a metal element, is used to close the chamber from beneath. Optionally, in this alternative, table 130, the conveyor belt and/or any other base on which the inspected items are placed is perforated or otherwise allows air passage, so that air jets may be directed at the items and/or samples may be collected from the inspected items from below. In an exemplary embodiment of the invention, air jets are directed at the inspected items from many directions in order to maximize the surface area from which samples are collected. In an exemplary embodiment of the invention, the conveyor belt comprises a plurality of cylinders which allow air to pass between the cylinders. Alternatively or additionally, the conveyor belt or table 130 comprises a net structure on which inspected items are placed.

In some embodiments of the invention, the conveyor belt and/or the mantle is formed of a material which does not absorb contaminant vapors or only minimally absorbs vapors, such as a repellant plastic. Alternatively, the conveyor belt and/or mantle is cleaned after each use, or after each use in which there was a detection, for example by air blasts. Further alternatively or additionally, the conveyor belt if formed of metal plates, for example welded steel wire trays. The metal plates are optionally moved along sprockets or a steel chain, so that no materials that absorb substantial amounts of contaminants are included in the conveyor belt. The conveyor belt may include a complete surface ring which leads the metal trays back to the starting point or the metal trays may be returned manually to their starting point.

Alternatively to placing inspected items 106 on a table, conveyor belt or other surface, inspected items 106 may be hung from above. For example, a crane may lift the inspected items and hold them while a chamber is formed around the items.

In some embodiments of the invention, system 100 includes a cleaning system 138 which cleans mantle 104, periodically. The cleaning may be performed before and/or after each inspection, hourly daily and/or at any other required times. Optionally, the cleaning is performed by injecting a liquid detergent toward mantle 104 and pumping out the liquid. Compressor 140 and/or blower 124 may be used thereafter to dry the mantle.

Alternatively or additionally, cleaning may be performed by injecting a liquid detergent, solvent and/or aerosol (optionally heated) through air pipes 132 and sucking the injected material out through pipes 122. Thus, in addition to cleaning mantle 104, the pipes are also cleaned. The cleaning process is optionally completed by injecting dry hot air through the system pipes.

External enclosure 102 optionally defines a sealed pressure chamber 148 having a controlled air pressure. Optionally, the air pressure in chamber 148 is larger than in chamber 136 so that mantle 148 is pushed close to inspected items 106. External enclosure 102 may comprise a rigid material or a flexible material as suitable. The air pressure of pressure chamber 148 is optionally held during operation at a desired value relative to the pressure of inspection chamber 136, so that mantle 104 does not change its orientation during operation of system 100. Optionally, the pressure difference between inspection chamber 136 and its surroundings is small and substantially constant, throughout an inspection session. In some embodiments of the invention, the air pressure within pressure chamber 148 is substantially equal to the atmospheric pressure, at the beginning of the vapor release stage of an inspection session. Alternatively, a higher or lower pressure is used. In some embodiments of the invention, external enclosure 102 is not included in system 100 and the external air pressure is atmospheric.

In some embodiments of the invention, the air pressure in chamber 136 is high, for example above 2 atmospheres, such that large amounts of air enter the inspected items. Optionally, at the end of the inspection session, the pressure is reduced in a decompression process and the released air is inspected for contaminants. Use of high pressures makes the decompression more effective. In some embodiments of the invention, tubes 160 lead from blower 124 and/or compressor 140 so as to control the air pressure within pressure chamber 148. Alternatively or additionally, a separate blower and/or compressor are used for pressure chamber 148. Further alternatively or additionally, tubes 132 and/or 122 and/or portions thereof are used to lead air into and/or out of pressure chamber 148.

Optionally, a controller 150 manages the operation of blower 124 and compressor 140, so as to control the relative air pressure between inspection chamber 136 and pressure chamber 148. An air pressure sensor 152 optionally provides pressure readings to controller 150 which accordingly adjusts the air flow into and out of inspection chamber 136. Alternatively or additionally, one or more other sensors are used and/or controller 150 operates according to a predetermined scheme without the use of sensors.

In some embodiments of the invention, air from compressor 140 is directed at inspected items 106 in the form of high speed air jets which aid in releasing vapors from the inspected items, as is now described.

Figure 2A:
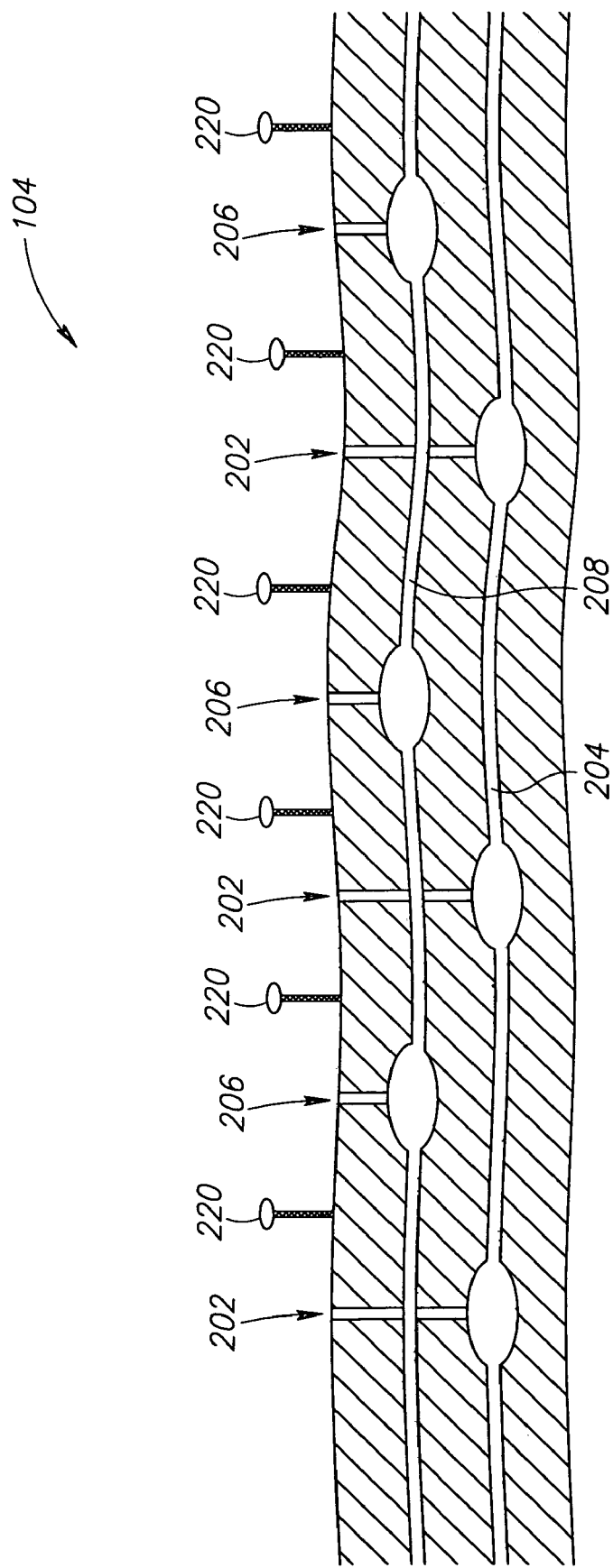
FIG. 2A is a cross-section view of a portion of a mantle of a vapor inspection system, in accordance with an exemplary embodiment of the invention.

Optionally, the air jets are at a speed of at least 10 meters per second. In some embodiments of the invention, the air jets have much higher speeds of even above 100 meters per second, when they enter the chamber and/or when they pass tangentially along the surface of the inspected items. As discussed above, in some embodiments of the invention, supersonic air jets are used, which have a speed of above about 330 meters per second. FIG. 2A is a cross-section view of a portion of mantle 104, in accordance with an exemplary embodiment of the invention. The upper side of mantle 104 in FIG. 2A is directed toward the inspected items 106. Mantle 104 optionally comprises a flexible and impervious material, for example a plastic, rubber (e.g., latex, silicon rubber), reinforced fabric or reinforced PVC. Mantle 104 may include a stretchable or non-stretchable material. Optionally, embedded within mantle 104 is a network of suction orifices 202 and conduits 204 which connect to blower 124 through air pipes 122 (FIG. 1B). Orifices 202 are optionally distributed throughout the area of mantle 104 so as to collect samples from different positions around inspected items 106. In some embodiments of the invention, orifices 202 are distributed evenly along the area of mantle 104. Alternatively, more orifices 202 are located toward the center of mantle 104 where they have a greater chance to collect samples from items 106. Alternatively to a plurality of suction orifices 202, only a single suction orifice is used.

In some embodiments of the invention, for simplicity, orifices 202 are constantly open and suction is controlled by blower 124. Alternatively, orifices 202 are controllable such that some of the orifices may be closed while others are open. The control of the flow through the orifices may be performed by closing the orifices at the end of the pipes or by valves along the pipes, not necessarily within the inspection chamber. In some embodiments of the invention, the valves are vacuum actuated valves. In some embodiments of the invention, each orifice 202 is controlled separately. Alternatively or additionally, orifices 202 may be controlled in groups. For example, different orifices 202 may be operated at different times according to a parameter of the currently applied vapor release method, for example the angle at which air jets are directed at items 106. Alternatively or additionally, orifices 202 are opened or closed according to the distance between the orifice and inspected items 106. In some embodiments of the invention, orifices 202 which are too close to, or too far from, inspected items 106 are closed, so that the air that they collect, which does not efficiently collect vapor does not dilute air collected through other orifices. Optionally, each orifice 202 (or group of orifices) is associated with a distance sensor which senses the distance between the orifice and inspected items 206. Alternatively or additionally, after removing the air from inspection chamber 104 (reaching the state in FIG. 1B) before applying vapor release methods, the air suction of orifices 202 is tested. Orifices that are inefficient and/or too efficient (they are far from the inspected items) are optionally closed.

In some embodiments of the invention, the suction is applied continuously throughout the inspection session or during relatively long periods, for example, after applying contaminant release measures. Alternatively, intermittent suction pulses are used to collect vapors from the inspected items. Such suction pulses add to the agitation of the inspected items, thus increasing the contaminant release.

A network of jet orifices 206, interconnected by air tubes 208, is optionally also embedded within mantle 104, separate from conduits 204 of suction orifices 202. Jet orifices 206 optionally connect to compressor 140, through air pipes 132. Jet orifices 206 are optionally used to direct air jets at inspected items 106. Orifices 206 are optionally distributed throughout the area of mantle 104 so as to inject air jets toward the inspected items from different positions around inspected items 106. In some embodiments of the invention, orifices 206 are distributed evenly along the area of mantle 104. Alternatively, more orifices 206 are located toward the center of mantle 104 where they have a greater chance to dislodge samples from items 106. Alternatively to a plurality of orifices 206, only a single jet orifice is used. In some embodiments of the invention, the distribution of orifices 202 and 206 is similar. Alternatively, suction orifices 202 are distributed differently from jet orifices 206. For example, in some embodiments of the invention, suction orifices 202 are intercalated, in order to reduce the tube length through which collected vapors need to pass on their way to collector 126.

In some embodiments of the invention, for simplicity, orifices 206 are constantly open and the air jets are controlled by activating and deactivating compressor 140. Alternatively, orifices 206 are controllable such that some of the orifices may be closed while others are open. Optionally, jet orifices 206 include valves that control the air pressure that comes from compressor 140. In some embodiments of the invention, each orifice 206 is controlled separately. Alternatively or additionally, orifices 206 may be controlled in groups. For example, different orifices 206 may be operated at different times according to a parameter of the currently applied vapor release method and/or the currently open suction orifices 202. Alternatively or additionally, jet orifices 206 are opened or closed according to the distance between the orifice and inspected items 106, optionally according to any of the methods described above with reference to suction orifices 202.

Alternatively or additionally to embedding conduits 204 and/or 208 within mantle 104, the air tubes may be attached on mantle 104, for example on an inner or outer surface of the mantle. Further alternatively or additionally, one or more air tubes pass through mantle 104 and are not attached to the mantle and/or are substantially perpendicular to the mantle. Optionally, a large number of air tubes enter the mantle, for example, above 20, 50 or even 100. Further alternatively or additionally, air tubes are directed at inspected items 106 from beneath (e.g., are placed on table 130, or beneath the table as described above) or from above. In some embodiments of the invention, a separate structure within inspection chamber 136, beneath mantle 104, carries the air tubes. Optionally, this structure also carries other vapor release apparatus, such as one or more heaters.

In some embodiments of the invention, mantle 104 comprises protruding legs 220, which prevent the mantle from closely touching the inspected items 106. Optionally, protruding legs 220 are positioned evenly throughout the area of mantle 104. Alternatively or additionally, protruding legs 220 are positioned with a higher density around suction orifices 202 in order to prevent the mantle from obstructing the flow of air into the suction orifices. In some embodiments of the invention, the length of protruding legs 220 is adjustable, for example according to the maximal dilution allowed in a specific scanning procedure. Alternatively or additionally, during an inspection session, the length of protruding legs 220 is adjusted to different lengths to maximize the suction and/or air jet effects.

Alternatively or additionally to protruding legs 220, the air pressure within chamber 136, relative to the air pressure between external enclosure 102 and mantle 104, prevents the mantle from attaching to inspected items 106. Further alternatively or additionally, a separate construction is used to prevent mantle 104 from touching inspected items 106.

As described above, in some embodiments of the invention, air jets are used to enhance vapor release from inspected items 106. Optionally, for simplicity, the air jets are at room temperature. Alternatively, the air jets include relatively hot air which is known to increase vapor release rates. In some embodiments of the invention, compressor 140 streams hot air into air pipes 132. Alternatively or additionally, one or more heaters heat the air while it passes through air pipes 132. Further alternatively or additionally, as described below, a heater within the chamber defined by mantle 104 heats the air from compressor 140 before it is shot at inspected items 106.

The jets are optionally directed at items 106 intermittently in pulses, for example 2-10 pulses per second. In some embodiments of the invention, the pulses are very short. Alternatively to short pulses, the pulses are relatively long, at least a few milliseconds for each pulse, requiring less complex valves. Further alternatively, the jets are constant and not pulsed. The term 'jet' used herein is meant to encompass all types of gas flow including both constant and intermittent flow. The intermittent flow is also referred to as bursts and/or pulses. The bursts may be repeated at a specific frequency or randomly. The term 'jet' also encompasses both ordinary straight jets and jets from flared outlets. The jets may be at substantially any velocity including supersonic velocities, constant velocities and varying velocities.

The air provided in the air jets is optionally taken from the atmosphere in the vicinity of vapor inspection system 100. Optionally, the air provided in the air jets by compressor 140 is cleaned, for example using an active carbon filter and/or a silica media filter, such that dirt and/or vapors are removed from the injected air. The filtering optionally reduces the noise level in trace analyzer 127, even if the dirt in the air is not of the same chemicals (or other target material) as being searched for. Alternatively or additionally, the air is preconditioned, for example by adding humidity to the air or drying the air in order to remove water vapors.

Alternatively to directing air jets at the inspected items, air jets may be directed in parallel to the surface of the inspected items, so as to cover a larger surface area.

Figure 2B:
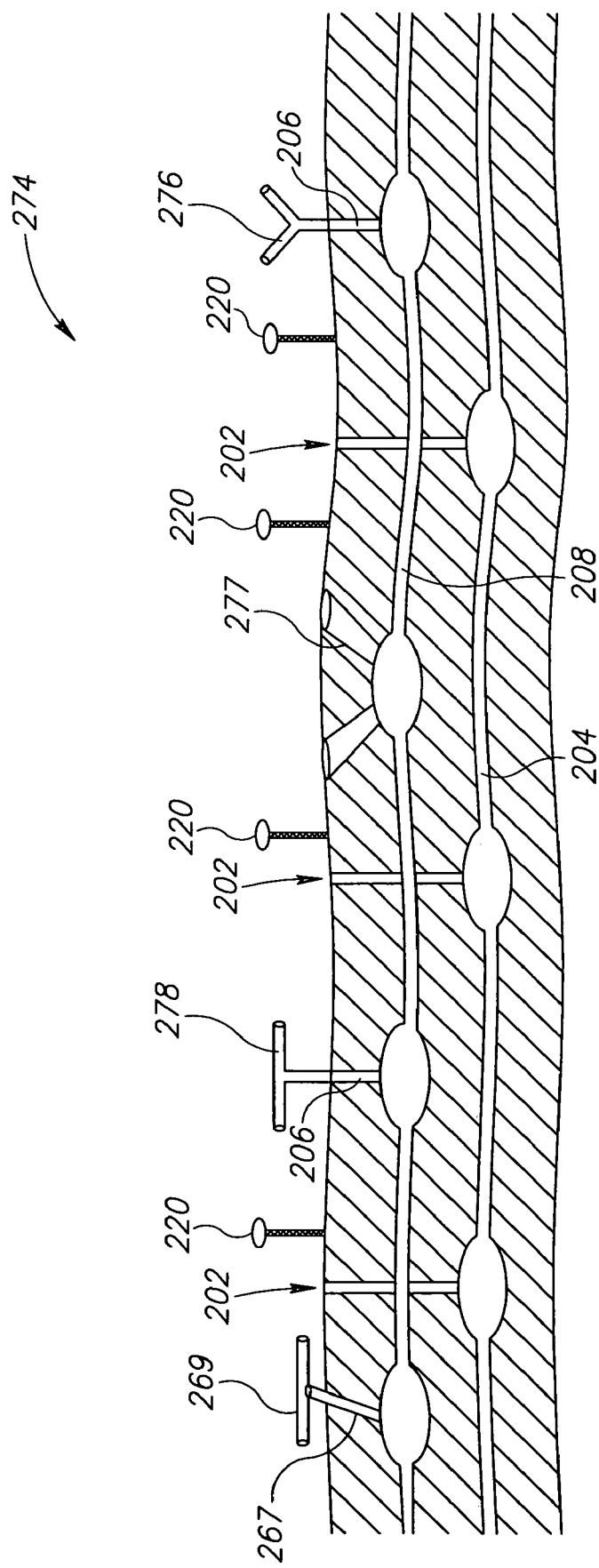
FIG. 2B is a cross-section view of a portion of a mantle of a vapor inspection system, in accordance with another exemplary embodiment of the invention.

FIG. 2B is a cross-section view of a portion of a mantle 274, in accordance with another exemplary embodiment of the invention. Mantle 274 is similar to mantle 104 of FIG. 2A, but includes bent extension pipes, which direct the air jets in a non perpendicular angle relative to the mantle, on at least some of jet orifices 206. As shown, mantle 274 includes pipes of a plurality of different shapes. A first pipe 277 has a V shape, within mantle 274, so as to direct air jets at the inspected items with an angle, for example of between 30-60°. Another pipe 276 has a Y shape, such that the slant is outside mantle 274, thus distancing the outlet of the air jets from the mantle to a greater extent. A third pipe 278 has a T shape, providing air jets parallel the inspected item. Although the pipes are shown as including two outlets, in some embodiments of the invention, the pipes may include only a single outlet or may include a plurality of outlets distributed evenly or unevenly around the circumference of the pipe. In some embodiments of the invention, mantle 274 does not include protruding legs 220, as pipes 276, 277 or 278 may serve to prevent mantle 274 from collapsing on the inspected items.

Alternatively to including different pipes 276, 277 and 278 at different locations along the mantle, the same type of pipe head is used for all jet orifices 206. In some embodiments of the invention, all jet orifices 206 have pipe heads mounted on them. Alternatively, not all the jet orifices 206 have pipe heads.

In some embodiments of the invention, mantle 104 includes one or more slanted pipes 267 within the mantle, which have a head 269 of any of the types discussed above. As described above with relation to pipe 277, the pipe may also not have a head.

Figure 3A:
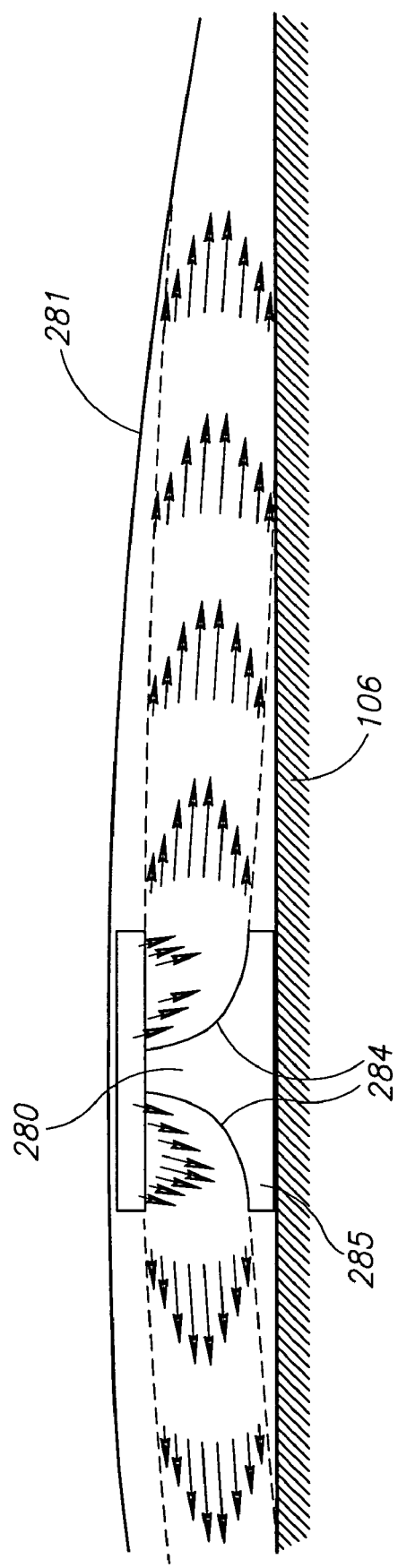
FIG. 3A is a schematic illustration of an air nozzle, within an inspection chamber, in accordance with an exemplary embodiment of the invention.

FIG. 3A is a schematic illustration of an air nozzle 280, within an inspection chamber, in accordance with an exemplary embodiment of the invention. As shown in FIG. 3A, a mantle 281 including at least one air nozzle 280 surrounds an inspected item 106. Air jets entering the inspection chamber through air nozzle 280 enter the nozzle perpendicular to mantle 281 and are deflected by a distal portion 285 of the nozzle, which prevents the air jets from impinging on the inspected item 106 directly. Distal portion 285 of nozzle 280 may have concave surfaces 284, as shown, or may have diagonal surfaces, square surfaces, convex surfaces and/or any other shape which is aerodynamically suitable. The air jets are optionally directed substantially parallel to inspected item 106, so as to remove contaminants from a large surface area. In some embodiments of the invention, the air jets are not entirely perpendicular to the items but rather are slightly directed toward the inspected items.

Nozzle 280 optionally touches inspected item 280 and optionally aids in preventing mantle 281 from collapsing onto the inspected item. Alternatively, nozzle 280 does not touch the inspected item and is held remote from the item by the air pressure within the inspection chamber, by small spacing legs and/or by any other spacing method.

In some embodiments of the invention, nozzle 280 is open all around in 360°, maximizing the surface area of the inspected item 106 affected by the air jets. In these embodiments, however, the energy of the air jets decreases relatively rapidly. Optionally, the number of nozzles 280 employed is chosen so as to cover at least a predetermined area (e.g., 50% or even 80%) of the surface of the inspected item 106 with effective air jets.

Alternatively, the nozzles may have a plurality of outlets around its circumference through which the air jets are dispensed. Optionally, the outlets may be closed, allowing control of the number of outlets through which the air jets are dispersed. Closing some of the outlets allows increasing the velocity of the air jets at the expense of affecting a smaller surface area.

Figure 3B:
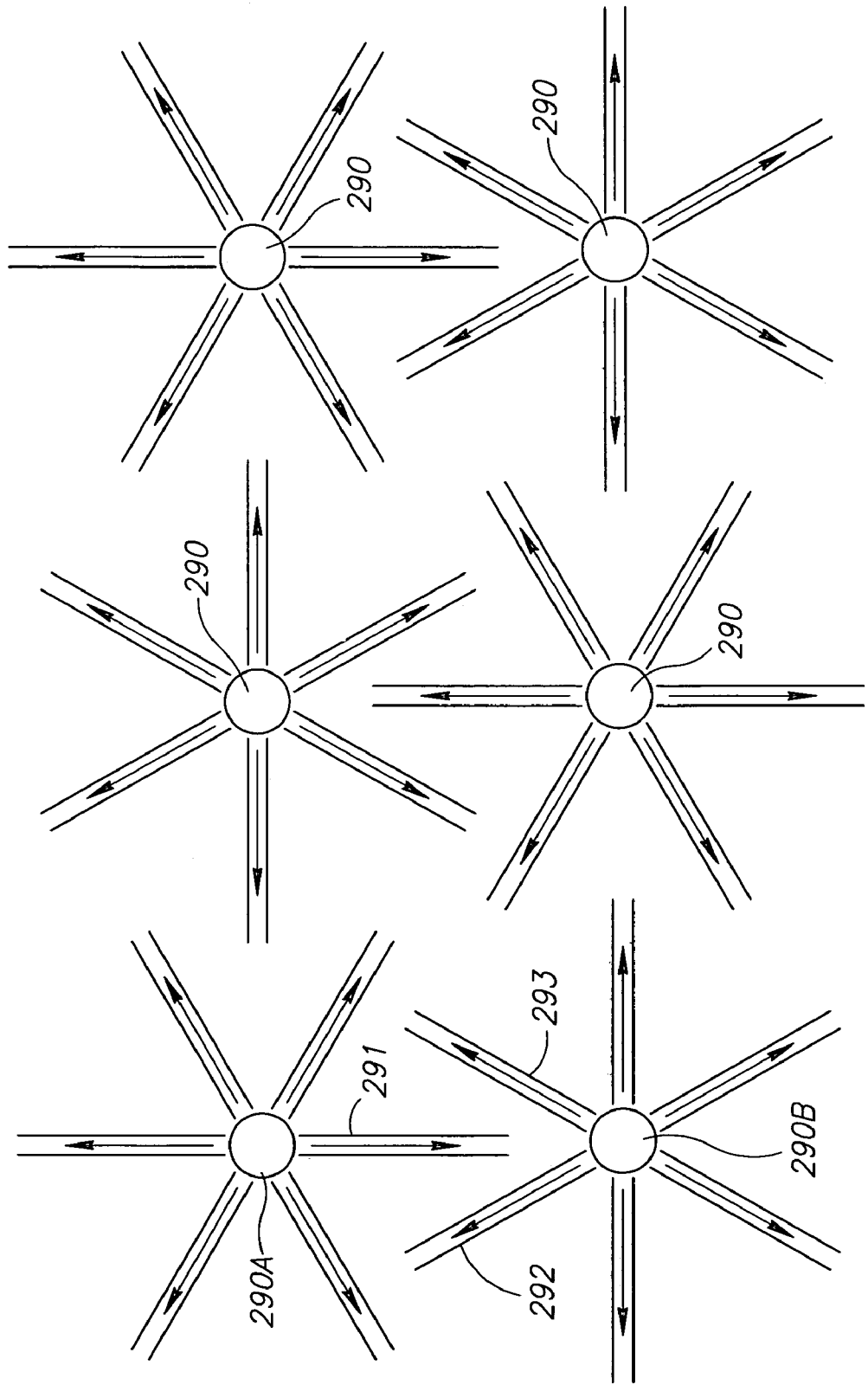
FIG. 3B is a schematic layout of nozzles, in accordance with an exemplary embodiment of the invention.

FIG. 3B is a schematic layout of nozzles 290, in accordance with an exemplary embodiment of the invention. As shown, each nozzle 290 lets out six air jets, evenly distributed around the circumference of the nozzle. Optionally, different nozzles are oriented differently in order to prevent overlap of different jets on a same surface area and/or to reduce the surface area not covered by any jets. For example, an air jet 291, from a first nozzle 290A, is directed toward a recess between air jets 292 and 293 of nozzle 290B. It will be understood that each nozzle 290 may have more or fewer outlets. In some embodiments of the invention, different nozzles have different numbers of outlets. Alternatively or additionally, the outlets of some or all of the nozzles are distributed unevenly around the circumference of the nozzle. Thus, air jets from one nozzle may be directed at uncovered zones in the vicinity of another nozzle.

In some embodiments of the invention, a combination of entirely open nozzles 280 and nozzles 290 having a predetermined number of outlets is used. This embodiment applies different air flows to different areas of the inspected item 106, and is especially advantageous on items for which it is not clear what type of jets are more effective.

In some embodiments of the invention, one or more nozzles 290 are rotatably mounted on the pipes leading the air from compressor 140 to the nozzle. During the generation of the air jets, nozzle 290 is rotated, so that the jets cover substantially the entire surface area surrounding the nozzle. Optionally, nozzle 290 rotates due to the release of the jets. Alternatively, nozzle 290 is actively rotated by a suitable motor. Nozzle 290 may be rotated throughout the entire release of the jets or may be rotated only during part of the jet release. In some embodiments of the invention, a break, for example controlled by controller 150, is used to prevent the rotation when so required.

In some embodiments of the invention, the air jets have a high pressure within the pipes and the pipes are properly configured, so that the jets generate shock waves when they are released into the chamber. Optionally, the pulses are at a pressure at least 1 atmosphere above the pressure within the chamber. In an exemplary embodiment of the invention, within the chamber a pressure of about 1 atmosphere is maintained, and the pulses are provided at pressures of between about 2-3 atmospheres. In another exemplary embodiment, the chamber is held at a pressure of about 2 atmospheres and the pulses are provided at between about 4-5 atmospheres. In still another embodiment, a pressure lower than 1 atmosphere is maintained in the chamber, making the production of shock waves much simpler. Optionally, the ports providing the jets have a relatively large diameter, suitable for generating shockwaves.

Figure 4:
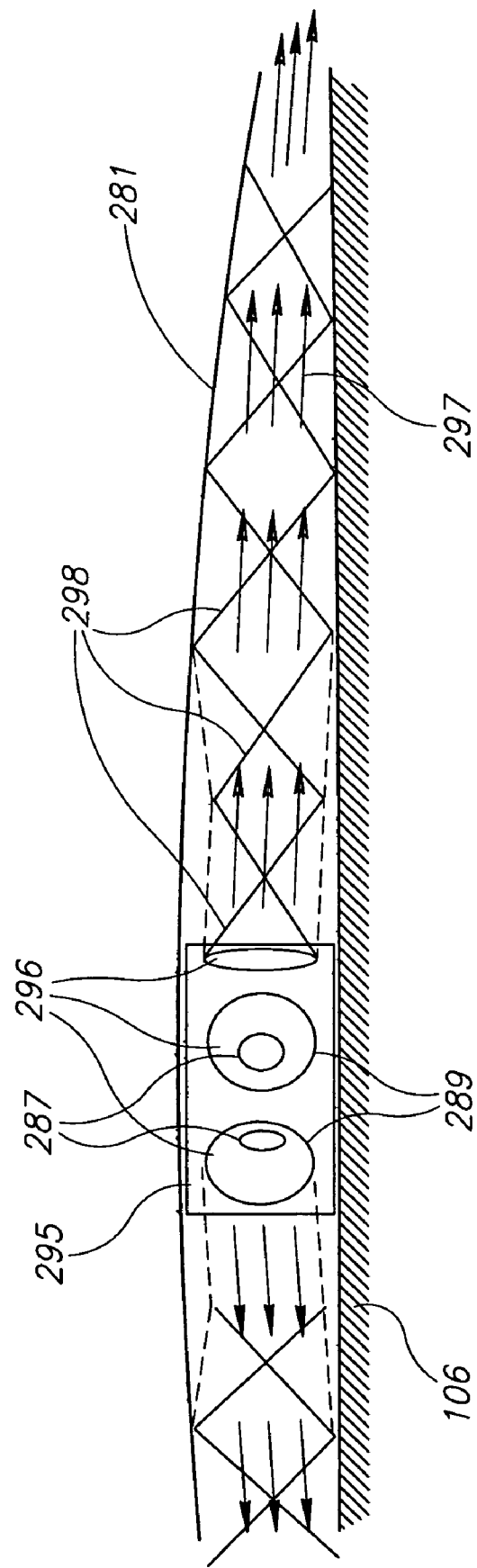
FIG. 4 is a schematic illustration of a supersonic air nozzle head, within an inspection chamber, in accordance with an exemplary embodiment of the invention.

FIG. 4 is a schematic illustration of a supersonic air nozzle head 295, within an inspection chamber, in accordance with an exemplary embodiment of the invention. As in FIG. 3A, an inspected item 106 is covered by a mantle 281. A supersonic nozzle head 295 includes one or more jet ports 296 (e.g., six) that eject supersonic air jets, which provide high speed shear flow 297 and alternating compression and expansion waves 298. The supersonic air jets are optionally generated by over expanding or under expanding the high speed flow of air using flared jet ports 296, which have an increasing diameter towards their outlets. In an exemplary embodiment of the invention, the pipe diameter along its length 287 is between about 3-3.5 mm (e.g., 3.15 mm) and flares to an outer diameter 289 of between about 7-10 mm (e.g., 8 mm), achieving an expansion of between about 2-3 times (e.g., 2.5). In some embodiments of the invention, a linear flaring is provided, for example, over a length of about 4-5 mm. Alternatively, any other flaring may be used, including a rounded flaring that expands more rapidly closer to the outlet and/or a stepped flaring that expands with a step function.

The acceleration of the air to supersonic velocities is due to the expansion of the air stream that is in the straight part of the nozzle at high pressure when it flows into the flared part of the nozzle. When the high velocity air flows into a low pressure zone, it forms a shock wave because the high pressure air flows faster. This shock wave reverberates when it is reflected from the walls of the enclosed volume, e.g., the surface of the inspected items 106 and the surface of the mantle.

In some embodiments of the invention, instead of using air to carry vapors from the inspected items 106, a different carrier gas, for example as described in, above mentioned, U.S. Pat. No. 6,324,927 is pumped by compressor 104 into the chamber and optionally at the inspected items. The different carrier gas may include a noble gas, such as argon and/or helium and/or may include relatively neutral gases, such as nitrogen and $CO_2$. Alternatively or additionally, a gas including a solvent, such as isopropyl alcohol and/or acetone vapors, is used, so that the carrier gas enhances the vapor release from inspected items 106. Further alternatively or additionally, a gas that has affinity to explosive materials, such as methyl amine, is used.

In some embodiments of the invention, jet orifices 206 all provide pulses of the air jets at substantially the same time. Alternatively, air jets from different jet orifices 206 are provided at different times. Optionally, air jets are provided through different jet orifices 206 according to a predetermined sequence, so as to induce a lateral air flow with the inspection chamber. Such a lateral air flow may aid in releasing vapor from the inspected items and/or in transfer of air samples to collector 126. In some embodiments of the invention, suction orifices 202 all suck air from the inspection chamber at the same time. These embodiments allow connection of all of suction orifices 202 through a single conduit 204. Alternatively, suction orifices 202 suck air at different times according to a predetermined scheme (optionally a scheme in common with the control of jet orifices 206), for example in order to induce air flow within the inspection chamber.

Other vapor releasing enhancement methods may be used alternatively or additionally to gas jets. In some embodiments of the invention, several cycles of increasing and decreasing the air pressure are applied within inspection chamber 136. The air pressure within external enclosure 102 is optionally adjusted accordingly so that mantle 104 does not move due to the pressure change. Alternatively or additionally to pressure changes, a high air pressure is formed in chamber 136 in order to force vapors out of the interior of inspected items 106.

In some embodiments of the invention, heaters heat the surface of the inspected item. Alternatively or additionally, light, sound (e.g., ultrasound, low frequency sound) and/or shock waves are directed at inspected items 106. In some embodiments of the invention, vapor release is enhanced by applying mechanical vibration to the inspected items, for example by vibrating table 130. Alternatively or additionally, inspected items 106 are placed within mantle 104 on a vibration unit. Further alternatively or additionally, inspection system 100 is mounted on a vehicle (e.g., ship, truck) which moves during operation so that inspected items 106 are vibrated. Further alternatively or additionally, any other method of inducing vapor release, known in the art, may be used.

Alternatively or additionally to sucking gas samples to a collector unit, trace analyzers and/or collection units are embedded within inspection chamber 136 and/or within the tubes leading gas toward collector 126. Embedded trace analyzers may be attached to mantle 104 on an inner surface, may be placed on table 130, may be hung from above and/or may be placed on a separate structure within mantle 104. Optionally, the embedded trace analyzers are small (having a diameter of about 1 inch and/or a weight of about 20 grams) so that they fit within the tubes (e.g., in a caving), conduits 204 and/or the chamber. Positioning trace analyzers within inspection chamber 136 and/or as close as possible thereto, reduces the distance that the vapors must pass on their way to analysis and hence reduces the chances of settling before reaching collector 126. Optionally, the embedded trace analyzers are connected through wires and/or a wireless connection to a control unit which provides indications to a human in charge of system 100.

In some embodiments of the invention, one or more embedded trace analyzers are used to detect specific chemicals which are hard to detect in collector 126. Alternatively or additionally, one or more embedded trace analyzers are used for additional accuracy beyond that provided by collector 126. For example, embedded trace analyzers may be of limited accuracy but may detect vapors which have less ability to be sucked through relatively long tubes. Alternatively, the embedded trace analyzers are used instead of collector 126. In some of these alternative embodiments, suction tubes are not used.

Figure 5:
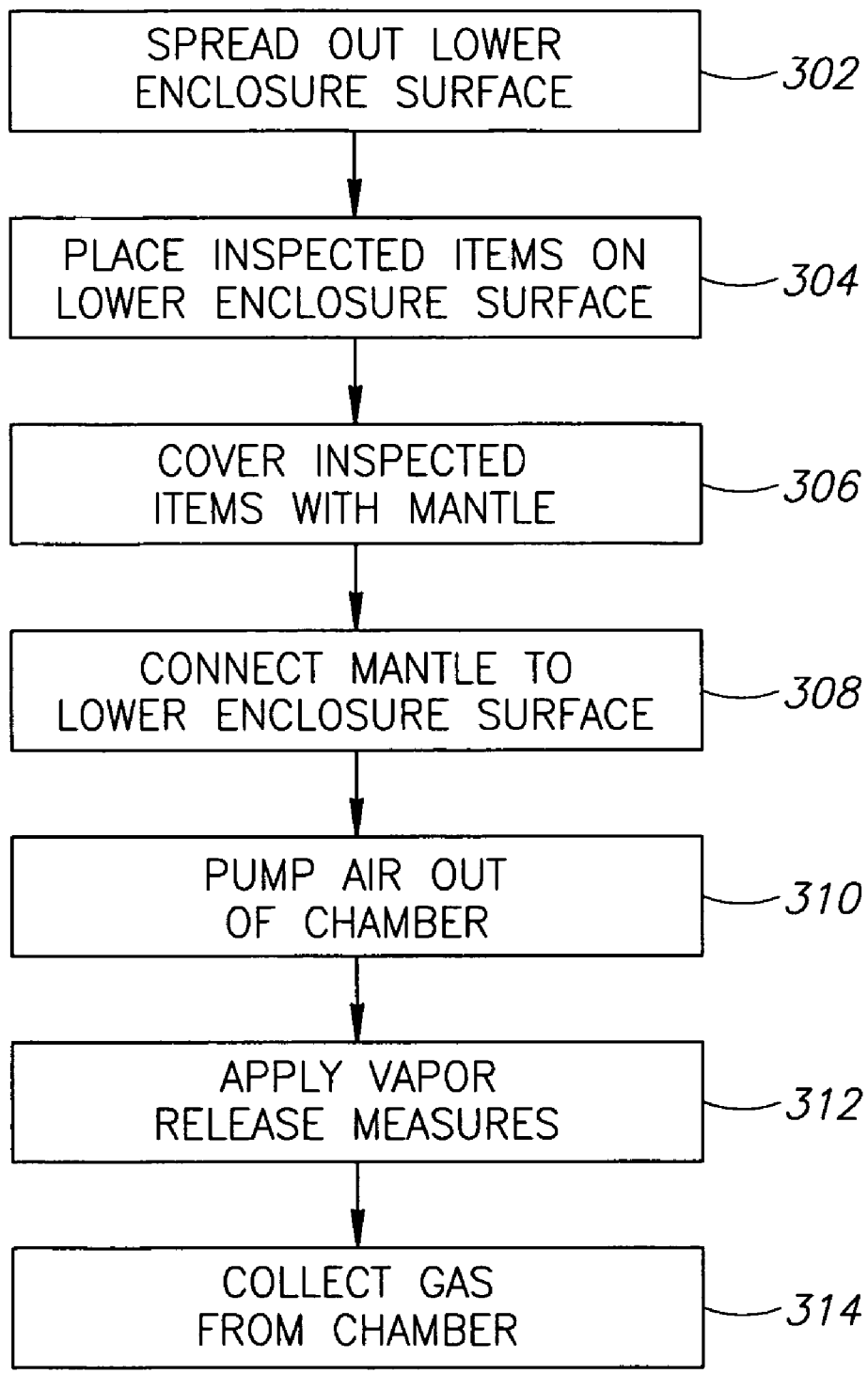
FIG. 5 is a flowchart of acts performed during an inspection session, in accordance with an exemplary embodiment of the invention.

FIG. 5 is a flowchart of acts performed during an inspection session, in accordance with an exemplary embodiment of the invention. Optionally, a lower enclosure surface is spread out (302) on table 130 or on any other surface. Inspected items 106 are then placed (304) on the lower enclosure surface. Mantle 104 is brought to cover (306) inspected items 106. Mantle 104 is optionally connected (308) to the lower enclosure surface in a manner which prevents air leakage from inspection chamber 136. Thereafter, as described above, air is pumped (310) out of inspection chamber 136 so that the size and air content of the chamber is minimized. Vapor release measures are applied (312) to inspected items 106 and in addition, air is collected (314) from inspection chamber 136.

Alternatively to forming chamber 136 from mantle 104 and a lower enclosure surface, chamber 136 may be defined by a single piece mantle and/or by a plurality of mantle pieces connected in a different form.

Figure 6A:
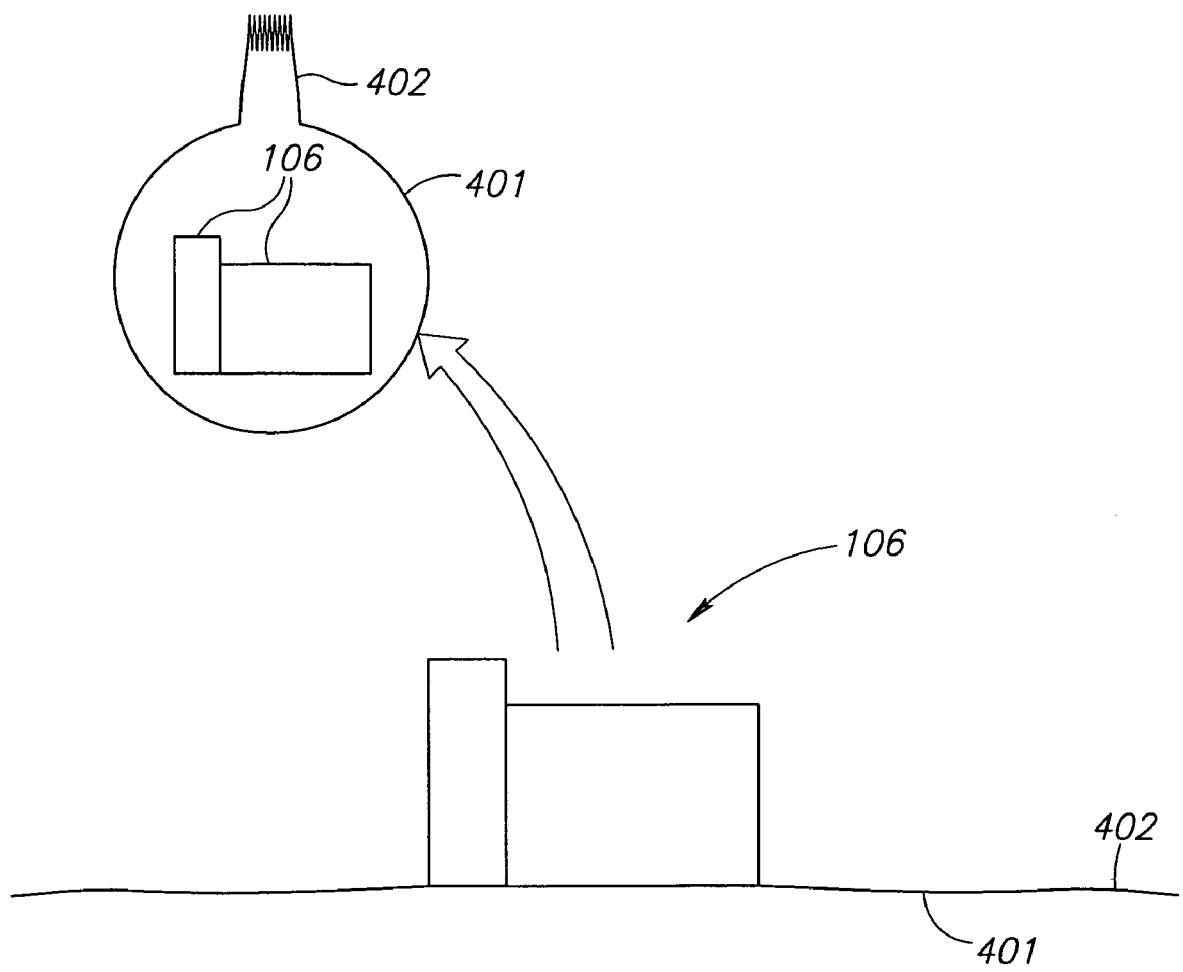
FIGS. 6A-6C schematically illustrate mantle structures, in accordance with exemplary embodiments of the invention.
Figure 6B:
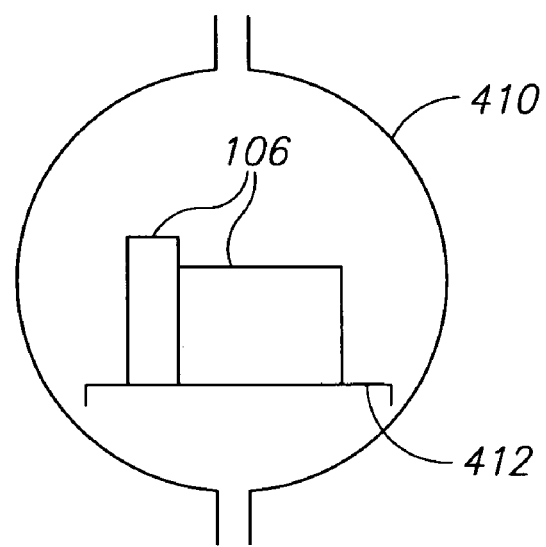
Figure 6C:
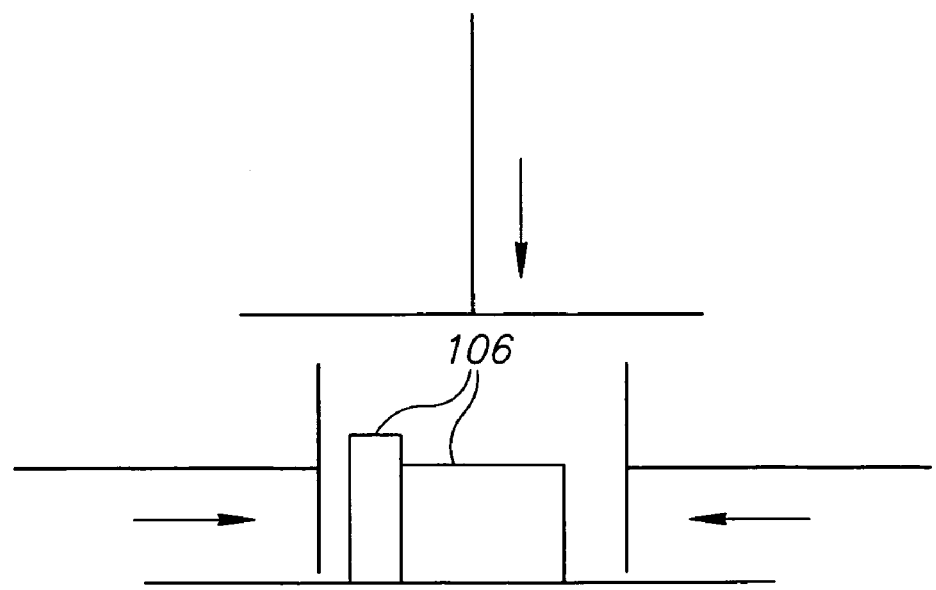

FIGS. 6A-6C schematically illustrate mantle structures, in accordance with exemplary embodiments of the invention. In FIG. 6A, a single-piece mantle 401 is shown. Optionally, inspected items 106 are placed on single-piece mantle 401 while it is spread out flat on a surface. Thereafter, ends 402 of mantle 401 are lifted and connected above inspected items 106, in order to form a sealed chamber.

In FIG. 6B, inspected items 106 are optionally placed on a table 412. Thereafter, right and left half mantles 410 are connected to each other forming a sealed chamber.

In FIG. 6C, the chamber is defined by walls, one or more of which are movable. After placement of inspected items 106, the walls of the chamber are moved toward the inspected items in order to limit the volume of the chamber. The side walls are optionally partially collapsible in order to allow the ceiling wall to move down toward inspected items 106.

Figure 7:
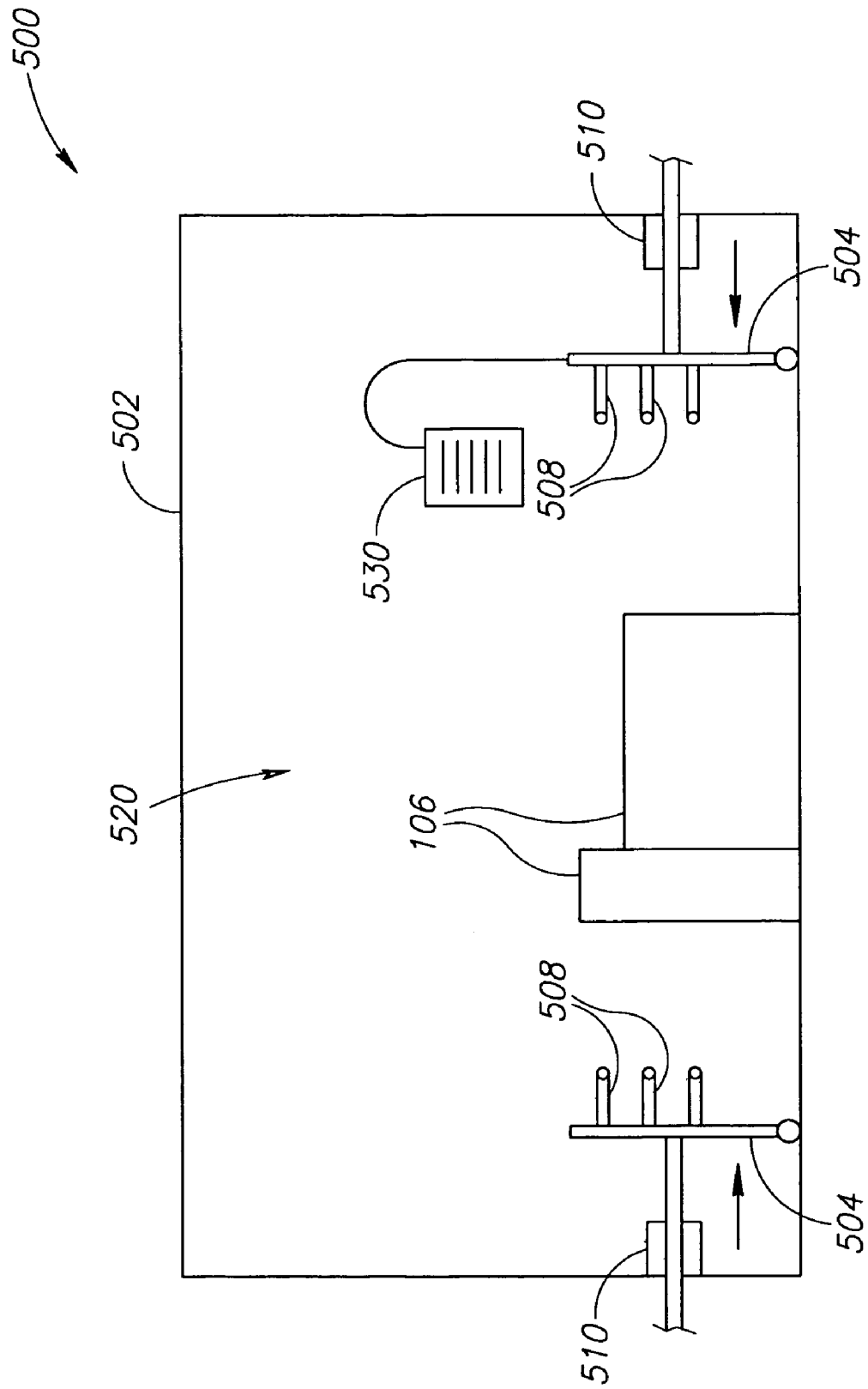
FIG. 7 is a schematic illustration of an inspection system, in accordance with an exemplary embodiment of the invention.

FIG. 7 is a schematic illustration of an inspection system 500, in accordance with an exemplary embodiment of the invention. System 500 optionally comprises a fixed casing 502, which defines an inspection chamber 520, in which inspected items 106 are placed, for inspection. In some embodiments of the invention, inspection 520 is sealed in a manner which prevents air from entering or escaping the chamber. Alternatively, the chamber may be operated while it is partially open, for example when it is not desired to seal the inspected items. One or more air tube structures 504 within inspection chamber 520 have an adjustable position. Air tube structures 504 optionally carry air tubes with suction and/or jet orifices 508 directed toward items 106.

In some embodiments of the invention, air tube structures 504 are mounted on adjustable length arms 510 which control the distance between the structures 504 and items 106. Optionally, after inspected items 106 are placed in chamber 520, structures 504 are automatically brought to a predetermined distance from the inspected items 106. The positions of structures 504 are optionally adjusted so that the distance between orifices 508 and inspected items 106 is optimal for collecting samples. Alternatively or additionally, during an inspection session, structure 504 is positioned at different locations, according to a predetermined operation program. Further alternatively or additionally, the position of structures 504 is adjusted according to inspection of air collected from the surroundings of the inspected items. For example, if in a certain positioning of structure 504 a high dust content or low vapor content is collected, the positioning of structure 504 is changed to achieve better results.

In some embodiments of the invention, the jet orifices are brought close to the inspected items at a position and/or angle which maximizes the contaminant release effect of the air jets. In an exemplary embodiment of the invention, the angle of the air jets are varied during a release session, so as to apply air jets at a wide span of angles, such that contaminants are released at least due to one of the angles. Optionally, in some of these embodiments, feedback is received on the effectiveness of the jets at each of the angles, and air jets at that angle are provided for a relatively long duration. In an exemplary embodiment of the invention, pressure and/or air velocity sensors are placed within the inspection chamber to determine the actual effect of the air jets within the chamber. Controller 150 optionally receives readings from the sensors and accordingly selects a best angle or other jet parameter (e.g., pulse rate).

It is noted that, as discussed above, also in the embodiment of FIG. 7 the air jets are not necessarily directed at the inspected items, but may be directed tangentially to the items. Optionally, the jet orifices are brought to corners of the inspected item, so as to direct air jets tangential to the surface from the corner of the item. Alternatively or additionally, T-shaped nozzle heads may be brought adjacent the inspected item, so as to release air jets tangential to the inspected items.

In some embodiments of the invention, a system-testing tracer chemical (identifiable by systems 100 or 500) is placed on the inspected items or in the injected air in order to serve as a testing trace material for the system. If the testing material is identified within a suitable range, the positioning of structures 504 is considered suitable for detection. Otherwise, the positioning of one or more structures 504 is changed and the test is repeated. Optionally, the tracer chemical is different from the chemicals (e.g., drugs, explosives) searched for, so that the tracer chemical does not interfere with the inspection of the luggage. Alternatively or additionally, the placement of the testing chemical is removed after the positioning of structure 504 is verified, so that the testing chemical does not interfere with detection of the vapors being searched for. Further alternatively or additionally, the testing chemical is used after samples for detection of the vapors searched for are collected, to determine if the results are valid. The tracer chemical may optionally be used for purposes other than adjusting the positioning of structures 504, for example for system development and/or proper operation monitoring.

Alternatively to using the system testing to determine proper placement of structures 504, the testing may be used for other reasons, such as selection of vibration frequencies, air jet attributes (e.g., pulse rate, angle, velocity) or other parameters of contaminant release systems. In some embodiments of the invention, the system testing is used to verify proper operation of the inspection system.

In some embodiments of the invention, a distance sensor is mounted on structures 504 to measure the distance between the structures and inspected items 106. Alternatively or additionally, structures 504 include protruding legs of a predetermined or adjustable length which aids in defining the distance between the structure 504 and items 106.

In some embodiments of the invention, a heater 530 is mounted on one or more of structures 504 or is otherwise positioned within chamber 520. Optionally, air jets from one or more orifices 508 are directed at heater 530 which heats the air jets and redirects the air toward inspected items 106. Optionally, the angle of heater 530 may be adjusted to achieve better vapor release results.

The inspection systems of the present invention may be used for substantially any items, including luggage and cargo. The system may be used to search for explosives, drugs, pests, pesticides, toxin contamination in agriculture produce, and/or any other chemical or biological substances which it may be desired to detect. The inspection systems of the present invention may be used in substantially any location, including, for example, airports and entrances to sensitive buildings.

In some embodiments of the invention, in order to enhance the ability to detect vapors from within the inspected items, one or more collection heads are inserted into the inspected items before the inspection session of the items begins. The collection heads may be used to further induce vapor release and/or to provide additional collection orifices from within the inspected items, as is now described.

Figure 8:
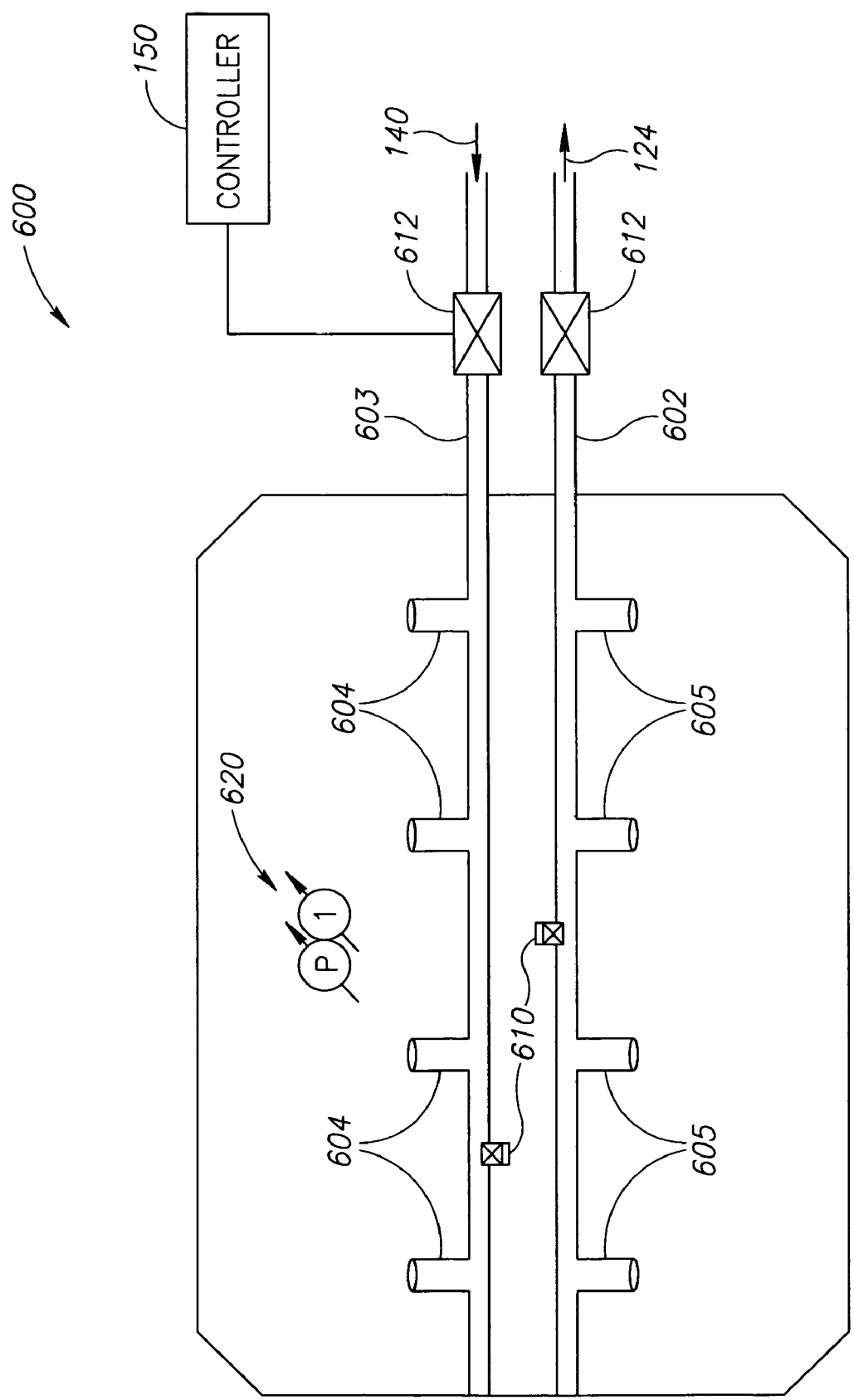
FIG. 8 is a schematic illustration of a collection head for vapors, in accordance with an exemplary embodiment of the invention.

FIG. 8 is a schematic illustration of a collection head 600, in accordance with an exemplary embodiment of the invention. Collection head 600 optionally includes one or more suction orifices 605, which connect through a suction tube 602 to collector 126 (FIG. 1B) and blower 124. Optionally, suction tube 602 and/or tube 122 only allow flow in one direction, so as to prevent loss of samples in case of decompression of collection head 600, for example due to power failure. In some embodiments of the invention, suction tube 602 and/or tube 122 include one way valves which prevent backflow. Alternatively or additionally, the pressure in collection head 600 and/or in the chambers to which the tubes lead is controlled, so as prevent flow in the incorrect direction.

Alternatively or additionally, collection head 600 includes one or more jet orifices 604, connected through a jet tube 603 to compressor 140. In some embodiments of the invention, one or more valves 610 are used to control the flow to or from one or more specific orifices an/or groups of orifices. Alternatively or additionally, one or more entrance valves 612 at the entrance to collection head 600 control all the jet and/or suction orifices together.

In some embodiments of the invention, air jets from jet orifices 604 are always directed in the same direction. Alternatively, the angle of release of air jets from one or more of jet orifices 604, such that the air jets may be directed in different directions during a single inspection session, without moving collection head 600. For example, jet orifices 604 may be rotatably mounted on collection head 600, so as to allow changes in the impinging direction of the air jets.

Jet orifices 604 and suction orifices 605 may operate in parallel with respective orifices in mantle 104 (FIG. 2A). Alternatively or additionally, the orifices of collection head 600 may operate at complimentary times to the orifices of mantle 104 in accordance with a single session plan. Further alternatively or additionally, the operation of the orifices of collection head 600 is controlled according to a plan independent of any operation plan of the orifices of mantle 104.

Optionally, collection head 600 includes additional and/or alternative vapor release enhancers. For example, collection head 600 may include a heater, a radiation source and/or a vibrator. Optionally, collection head 600 comprises a rigid cassette that does not change its volume. Alternatively, collection head 600 comprises an inflatable pillow, which may be inflated and/or deflated in order to induce vibrations. Further alternatively or additionally, collection head 600 comprises an internal mechanical and/or electrical motor and/or springs which induce vibrations upon command. Further alternatively or additionally, collection head 600 includes other vibration mechanisms, such as a mechanism for inducing vibration by directing gas jets in one or more directions.

In some embodiments of the invention, collection head 600 includes one or more sensors 620, for example, temperature and/or pressure sensors, whose readings are provided to controller 150. Controller 150 optionally controls the operation of collection head 600, setting one or more vapor release and/or collection parameters, according to the readings of the sensors.

In some embodiments of the invention, as described above, collection head 600 operates in conjunction with mantle 104 or system 500. In these embodiments, collection head 600 may be used for both sample collection and enhancement of vapor release or may be used for only one of the tasks, the other task being carried out by mantle 104.

Alternatively or additionally, collection head 600 may be operated alone without mantle 104. For example, an inspection session may include a first stage including placing an inspection item 106 within chamber 136 and collecting gas samples using mantle 104, and a second stage in which samples are collected by collection head 600 inserted into the inspected item. Optionally, during the second stage, a human operator may hold collection head 600 and move it around within the inspected item. In some embodiments of the invention, collection head 600 includes a handle (not shown) for human manipulation of the collection head.

As described above, gas samples from collection head 600 are provided to the same collector 126 as the gas samples from mantle 104. In some embodiments of the invention, however, different collectors may be used for collection head 600 and for mantle 104. The different collectors are optionally connected to the same trace analyzer, which receives samples from the different collectors in parallel or at different times. Alternatively, the different collectors are connected to different trace analyzers, which test for the same chemicals or for different chemicals.

In some embodiments of the invention, collection head 600 serves as a dual purpose apparatus which may be used both for item inspection as described above and for inspection of people. Optionally, when used to inspect people, an operator hold collection head 600 and passes it around the inspected person. In some embodiments of the invention, when used to inspect people, when or more operation parameters of collection head 600 are adjusted accordingly, for example, the heat of the air jets (so as not to cause discomfort to the inspected person) and/or the direction of the air jets (toward the inspected person). Optionally, collection head 600 has a plurality of operation modes. For example, a first operation mode is used for inspecting items where collection head 600 is within the item and is substantially surrounded by the item. In the first operation mode, air jets are optionally transmitted in all directions (according to the distribution of orifices). In a second operation mode, collection head 600 is used to inspect a person. In the second operation mode, air jets are directed only in a single direction.

In some embodiments of the invention, collection head 600 includes apparatus other than required for gas sample collection. For example, collection head 600 may include a metal detector. The metal detector may be operated during the second operation mode when used to inspect persons.

Figure 9:
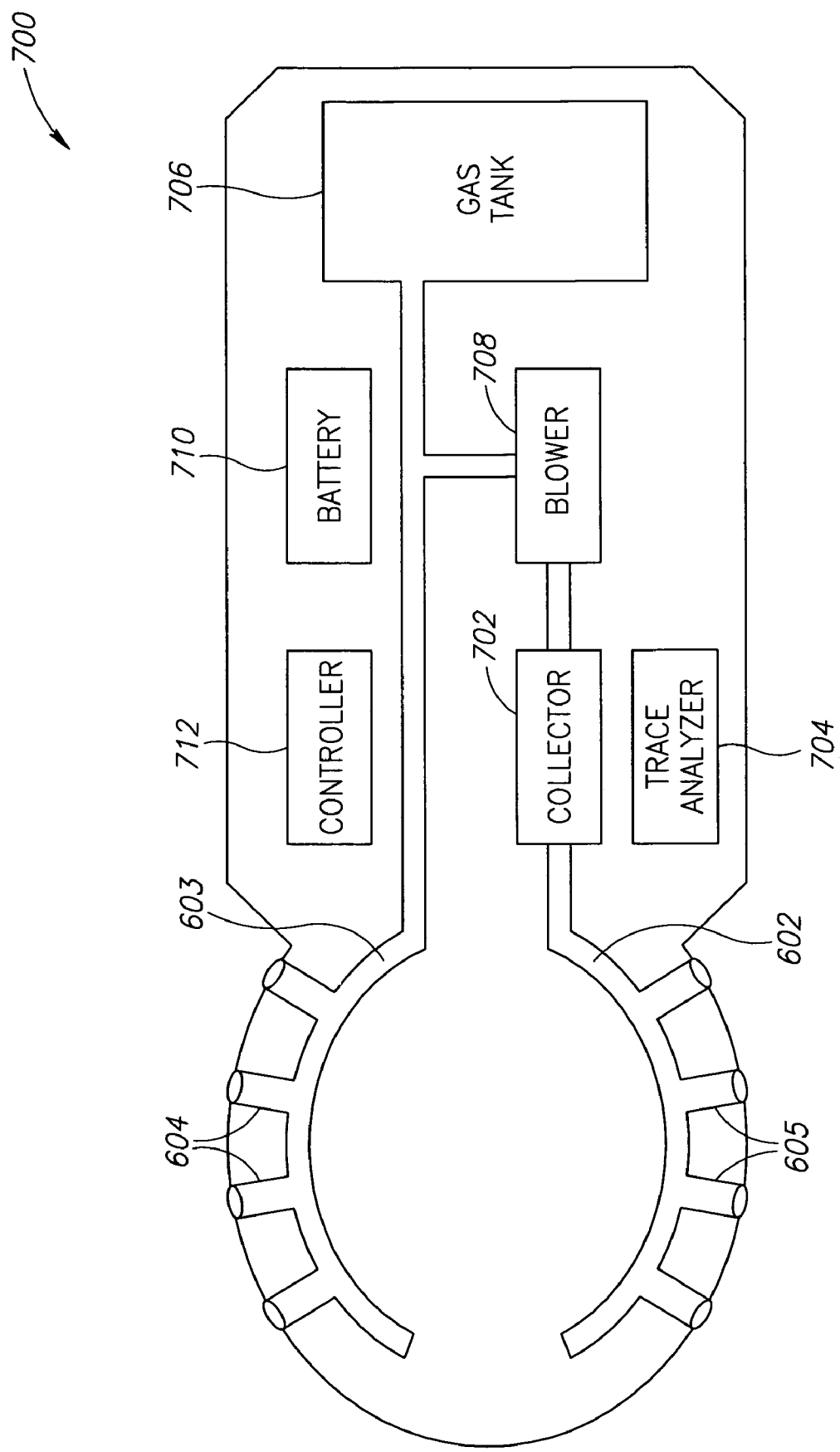
FIG. 9 is a schematic illustration of a self contained vapor collection unit, in accordance with an exemplary embodiment of the invention.

FIG. 9 is a schematic illustration of a self contained vapor collection unit 700, in accordance with an exemplary embodiment of the invention. Collection unit 700 is optionally similar to collection head 600, but is self contained and is not connected through air tubes to an external system. Collection unit 700 optionally includes a collector 702, a trace analyzer 704 and a blower 708 which sucks samples through suction orifices 605 into collector 702. Alternatively, for example in order to reduce the size of collection unit 700, trace analyzer 704 is not included in the collection unit. Instead, collection unit 700 is connected after a collection session to an external trace analyzer (not shown) or collector 702 is removed from collection unit 700 and connected to an external trace analyzer. Optionally, collection unit 700 includes a gas tank 706 which contains gas in high pressure, and serves as a source for gas jets. Alternatively or additionally, blower 708 (or a separate compressor) is used to generate gas jets from gas external to collection unit 700. It is noted that additional vapor release apparatus, for example any of those described above with relation to collection head 600, may also be included in collection unit 700.

A battery 710 optionally provides power for operation of collection unit 700. Alternatively, collection unit 700 is connected to an external power line. An internal controller 712 optionally controls the operation of collection unit 700 according to pre-programmed instructions. Alternatively or additionally, internal controller 712 is connected through wires or wirelessly to an external controller.

Collection unit 700 is optionally placed in an inspected item for an inspection procedure. In some embodiments of the invention, collection unit 700 is used alone and not in conjunction with system 100 or system 500 described above. For example, in transferring mail or cargo, one or more collection units 700 are placed in the mail bag or cargo casing before the transfer and is removed after the transfer. When the collection unit 700 is removed from the cargo casing, its contents are checked for chemicals being searched for. Alternatively or additionally, an alarm signal may be wirelessly transmitted to a control station if a chemical of interest is found within the inspected item. Optionally, the jogging of the cargo and/or the long term placement of unit 700 with the cargo is relied upon to release vapors from the cargo, such that the amount of enhancement vapor release measures applied by collection unit 700 may be reduced or not used at all. Alternatively or additionally, collection unit 700 may be used for short periods. For example, collection unit 700 may be inserted to the inspected item, operated, and then immediately removed and connected to a trace analyzer. Optionally, in parallel to connecting collection unit 700 to the external trace analyzer, battery 710 is charged such that there is sufficient power to perform additional collection sessions. Alternatively or additionally, between collection sessions, collection unit 700 is cleaned.

In some embodiments of the invention, for example for inspecting large inspected items, a plurality of collection units are inserted into the inspected item.

Collection unit 700 may operate continuously until it is removed from the inspected items or until its power source is drained out. Alternatively, collection unit 700 operates according to a pre-configured operation program stored in controller 712. Further alternatively or additionally, collection unit 700 operates according to commands transmitted from an external unit with which it operates in coordination. For example, collection unit 710 may operate in coordination with system 100 described above.

Collection unit 700, as shown, includes both vapor collection means and vapor release enhancement means. In some embodiments of the invention, however, a collection unit which only collects vapors and does not induce vapor release may be used. Such a collection unit may be lighter, cheaper and smaller. Alternatively or additionally, a vapor release enhancement unit which does not collect vapors is used.

In some embodiments of the invention, both a vapor release collection means and a vapor release enhancement unit are placed within the inspected item, together and/or at different places or ends in the inspected item. Alternatively or additionally, for example in use with system 100, only a vapor collection unit or only a vapor enhancement unit, may be used. As described above, a collection unit may be used on its own and, for example, the transport of the inspected items may be used to induce vapor release.

In an exemplary embodiment of the invention, after inserting a collection unit to the inspected item, the inspected item is inserted into chamber 136 in order to induce vapor release. In other embodiments of the invention, a vapor release unit is inserted into the inspected item for operation while the inspected item is within chamber 136.

It will be appreciated that the above described methods may be varied in many ways, including, changing the order of steps, and/or performing a plurality of steps concurrently. It should also be appreciated that the above described description of methods and apparatus are to be interpreted as including apparatus for carrying out the methods, and methods of using the apparatus. The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims.

The invention claimed is:

1. A method for removing samples of a substance from a surface of an item for inspection, the method comprising:
    surrounding an item for inspection by an enclosure, wherein at least a portion of the enclosure is flexible;
    conforming the flexible portion of the enclosure to the size of the item for inspection by sucking air out of the enclosure through at least one second conduit;
    directing a gas flow into the enclosure through at least one first conduit embedded in the flexible portion, after the flexible portion conforms, via an outlet from the at least one first conduit into the enclosure adjacent the surface, wherein the outlet is configured for directing the gas flow as it leaves the outlet at an angle that is not perpendicular to the flexible portion adjacent to the outlet; and
    extracting gas samples out of the enclosure through the at least one second conduit embedded within the flexible portion.

2. A method according to claim 1, wherein the flexible portion of the enclosure comprises a flexible mantle.

3. A method according to claim 1, comprising analyzing the gas samples for traces of one or more particulates.

4. A method for removing samples of a substance from a surface of an item for inspection, the method comprising:
surrounding an item for inspection by an enclosure, wherein at least a portion of the enclosure is flexible;
conforming the flexible portion of the enclosure to the size of the item for inspection;
directing a gas flow into the enclosure through at least one first conduit embedded in the flexible portion, after the flexible portion conforms, via an outlet from the at least one first conduit into the enclosure adjacent the surface, wherein the outlet is configured for directing the gas flow as it leaves the outlet at an angle that is not perpendicular to the flexible portion adjacent to the outlet; and
extracting gas samples out of the enclosure through at least one second conduit embedded within the flexible portion,
wherein the gas flow through the at least one outlet is at a speed of at least 10 meters per second.

5. A method according to claim 4, wherein the at least one outlet is configured for directing the gas flow in a direction tangential to the surface of the item for inspection.

6. A method according to claim 4, wherein the gas flow through the at least one outlet is at a speed of at least 100 meters per second.

7. A method according to claim 4, wherein the at least one outlet is fluidly connected to at least one nozzle comprising a plurality of outlets dispersed around a circumference of the at least one nozzle.

8. A method according to claim 4, wherein the angle is at least 30° with respect to a perpendicular to the flexible portion through which the outlet is formed.

9. A method according to claim 4, wherein the gas flow through the at least one outlet is at a speed of at least 330 meters per second.

10. A method according to claim 4, wherein the gas flow hits the inspected item with an angle of less than 60 degree to the surface of the inspected item.

11. A method according to claim 4, wherein the gas flow hits the inspected item with an angle of 30 degree to the surface of the inspected item.

12. A system for removing samples of a substance from the surface of an item for inspection comprising:
an enclosure comprising at least one mantle, the mantle configured for conforming to a size of an item for inspection placed within the enclosure, the mantle including at least one first conduit embedded within the mantle configured for directing gas flow into the enclosure and at least one second conduit embedded within the mantle configured for directing gas flow out of the enclosure;
at least one outlet fluidly connected to the at least one first conduit configured for directing the gas flow in a direction that has a component parallel to a surface of the item for inspection adjacent the outlet;
at least one inlet fluidly connected to the at least second conduit configured for extracting gas samples out of the enclosure;
wherein the at least one outlet is adapted to eject a supersonic jet.

13. A system for removing samples of a substance from the surface of an item for inspection comprising:
an enclosure comprising at least one mantle, the mantle configured for conforming to a size of an item for inspection placed within the enclosure, the mantle including at least one first conduit embedded within the mantle configured for directing gas flow into the enclosure and at least one second conduit embedded within the mantle configured for directing gas flow out of the enclosure;
at least one outlet fluidly connected to the at least one first conduit configured for directing the gas flow in a direction that has a component parallel to a surface of the item for inspection adjacent the outlet;
at least one inlet fluidly connected to the at least second conduit configured for extracting gas samples out of the enclosure;
wherein the outlet is adapted to eject jets at a speed of at least 10 meters per second.

14. A system according to claim 13 wherein the at least one outlet is adapted to eject jets at a speed of at least 100 meters per second.

15. A system according to claim 13 wherein the outlet is adapted to eject jets at a speed of at least 330 meters per second.

16. A system according to claim 13, wherein the at least one outlet has at least one flared outlet.

17. A system according to claim 13, wherein the at least one outlet has a plurality of outlets evenly dispersed around its circumference.

18. A system according to claim 13, wherein the at least one outlet is adapted to touch the surface of the item for inspection within the chamber during an inspection session.

19. A system according to claim 13 wherein the outlet is adapted to direct gas flow substantially parallel to the surface of the item for inspection.

20. A system according to claim 13, wherein at least one conduit is fluidly connected to a plurality of outlets.

21. A system according to claim 13, wherein the at least one outlet is positioned such that the gas flow is not directed at the item for inspection.

22. A system according to claim 13, wherein the at least one outlet is configured for directing gas flow toward the inspected item with an angle of less than 60 degree to the surface of the inspected item.

23. A system according to claim 13, wherein the at least one outlet is configured for directing gas flow toward the inspected item with an angle of 30 degree to the surface of the inspected item.

24. A system for removing samples of a substance from the surface of an item for inspection comprising:
an enclosure comprising at least one mantle, the mantle configured for conforming to a size of an item for inspection placed within the enclosure, the mantle including at least one first conduit embedded within the mantle configured for directing gas flow into the enclosure and at least one second conduit embedded within the mantle configured for directing gas flow out of the enclosure;
at least one outlet fluidly connected to the at least one first conduit configured for directing the gas flow in a direction that has a component parallel to a surface of the item for inspection adjacent the outlet;
at least one inlet fluidly connected to the at least second conduit configured for extracting gas samples out of the enclosure;
wherein the at least one second conduit is fluidly connected to a plurality of inlets distributed throughout an area of the enclosure, the inlets adapted to remove the gas samples from different positions around the items for inspection.

25. A system according to claim 24, comprising an analysis unit adapted to determine whether the gas samples include one or more particulates.

26. A system according to claim 24, wherein the mantle comprises a stretchable material.

27. A system according to claim 24, comprising at least one spacer configured for preventing the mantle from touching the item for inspection over a substantial area.

28. A system according to claim 24, wherein air pressure in the chamber is controlled to achieve a desired distance between the at least one mantle and the item for inspection.

* * * * *